US007476687B2

(12) United States Patent
Dantanarayana et al.

(10) Patent No.: US 7,476,687 B2
(45) Date of Patent: Jan. 13, 2009

(54) SUBSTITUTED FURO[2,3-G]INDAZOLES FOR THE TREATMENT OF GLAUCOMA

(75) Inventors: Anura P. Dantanarayana, Kandy (LK); Jesse Albert May, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 314 days.

(21) Appl. No.: 10/580,528

(22) PCT Filed: Nov. 24, 2004

(86) PCT No.: PCT/US2004/039661

§ 371 (c)(1),
(2), (4) Date: May 24, 2006

(87) PCT Pub. No.: WO02/098350

PCT Pub. Date: Dec. 12, 2002

(65) Prior Publication Data

US 2007/0135430 A1    Jun. 14, 2007

Related U.S. Application Data

(60) Provisional application No. 60/525,635, filed on Nov. 26, 2003.

(51) Int. Cl.
*A01N 43/56* (2006.01)
(52) U.S. Cl. .................. 514/406; 548/373.1; 424/78.04
(58) Field of Classification Search ........................ None
See application file for complete search history.

(56) References Cited

U.S. PATENT DOCUMENTS

| | | | |
|---|---|---|---|
| 4,690,931 A | 9/1987 | Wick et al. | 514/317 |
| 5,011,846 A | 4/1991 | Gittos et al. | 514/294 |
| 5,151,444 A | 9/1992 | Ueno et al. | 514/530 |
| 5,290,781 A | 3/1994 | Espino et al. | 514/259 |
| 5,296,504 A | 3/1994 | Stjernschantz et al. | 514/530 |
| 5,352,708 A | 10/1994 | Woodward et al. | 514/729 |
| 5,422,368 A | 6/1995 | Stjernschantz et al. | 514/530 |
| 5,494,928 A | 2/1996 | Bös | 514/415 |
| 5,538,974 A | 7/1996 | Ogawa et al. | 514/253 |
| 5,561,150 A | 10/1996 | Wichmann | 514/406 |
| 5,571,833 A | 11/1996 | Kruse et al. | 514/414 |
| 5,578,612 A | 11/1996 | Macor et al. | 514/323 |
| 5,646,173 A | 7/1997 | Bös et al. | 514/411 |
| 5,652,272 A | 7/1997 | Ogawa et al. | 514/652 |
| 5,693,654 A | 12/1997 | Birch | 514/323 |
| 5,874,477 A | 2/1999 | McConnell et al. | 514/657 |
| 5,889,052 A | 3/1999 | Klimko et al. | 514/530 |
| 5,902,815 A | 5/1999 | Olney et al. | 514/285 |
| 6,107,324 A | 8/2000 | Behan et al. | 514/406 |
| 6,245,796 B1 | 6/2001 | Maeno et al. | 514/403 |
| 6,660,870 B1 | 12/2003 | Ruskinko et al. | 548/307.4 |
| 6,664,286 B1 | 12/2003 | May et al. | 514/415 |
| 6,696,476 B2 | 2/2004 | Chen et al. | 514/403 |
| 6,806,285 B1 | 10/2004 | May et al. | 514/416 |
| 6,881,749 B2 | 4/2005 | Chen et al. | 514/403 |
| 6,884,816 B2 | 4/2005 | May et al. | 514/405 |
| 6,927,233 B1 | 8/2005 | May et al. | 514/403 |
| 6,933,392 B2 | 8/2005 | May et al. | 548/359.1 |
| 6,956,036 B1 | 10/2005 | May et al. | 514/233.8 |
| 6,960,579 B1 | 11/2005 | May et al. | 514/226.5 |
| 6,960,608 B2 | 11/2005 | May et al. | 514/405 |
| 6,989,445 B2 | 1/2006 | Dantanarayana et al. | 544/101 |
| 6,998,489 B2 | 2/2006 | Conrow et al. | 548/362.5 |
| 7,005,443 B1 | 2/2006 | May et al. | 514/403 |
| 7,005,448 B2 | 2/2006 | May | 514/469 |
| 7,012,090 B1 | 3/2006 | May et al. | 514/411 |
| 7,060,704 B2 | 6/2006 | May et al. | 514/254.09 |
| 7,071,225 B2 | 7/2006 | Hellberg et al. | 514/443 |
| 7,129,257 B1 | 10/2006 | Dantanarayana et al. | 514/360 |
| 7,208,512 B2 | 4/2007 | Feng et al. | 514/397 |
| 7,268,131 B2 | 9/2007 | Dantanarayana et al. | 514/228.5 |
| 7,285,553 B2 | 10/2007 | May et al. | 514/255.03 |
| 2003/0181504 A1 | 9/2003 | May et al. | 514/406 |
| 2003/0203912 A1 | 10/2003 | May et al. | 514/249 |
| 2003/0207890 A1 | 11/2003 | Collier, Jr. et al. | 514/252.15 |
| 2005/0171190 A1 | 8/2005 | May et al. | 514/450 |
| 2005/0209314 A1 | 9/2005 | Hellberg et al. | 514/456 |
| 2005/0256129 A1 | 11/2005 | Collier, Jr. et al. | 514/252.15 |
| 2006/0052431 A1 | 3/2006 | May et al. | 514/403 |
| 2006/0052613 A1 | 3/2006 | Delgado et al. | 548/361.1 |
| 2006/0069096 A1 | 3/2006 | Dantanarayana et al. | 514/235.5 |
| 2006/0073172 A1 | 4/2006 | Schneider et al. | 424/400 |

(Continued)

FOREIGN PATENT DOCUMENTS

EP    0 771 563 B1    10/1996

(Continued)

OTHER PUBLICATIONS

Arrault et al., "New Synthetic Approach to Naphtho[1,2-*b*]furan and 4'-Oxo-Substituted Spiro[cyclopropane-1,1'(4'*H*)-naphthalene]Derivatives," *Helvetica Chimica Acta*, vol. 84, pp. 2198-2211 (2001).

(Continued)

*Primary Examiner*—Michael G Hartley
*Assistant Examiner*—Nissa M. Westerberg
(74) *Attorney, Agent, or Firm*—Patrick M. Ryan

(57) ABSTRACT

Substituted furo[2,3-g]indazoles for lowering intraocular pressure and treating glaucoma are disclosed.

4 Claims, No Drawings

U.S. PATENT DOCUMENTS

| | | | |
|---|---|---|---|
| 2006/0122251 A1 | 6/2006 | Chen et al. | 514/406 |
| 2006/0211700 A1 | 9/2006 | May et al. | 514/250 |
| 2007/0072920 A1 | 3/2007 | Hellberg et al. | 514/365 |
| 2007/0293475 A1 | 12/2007 | Mohapatra et al. | 514/217.01 |
| 2008/0033183 A1 | 2/2008 | Conrow | 548/359.5 |
| 2008/0033184 A1 | 2/2008 | Delgado et al. | 548/362.5 |
| 2008/0058533 A1 | 3/2008 | Delgado et al. | 548/358.5 |

FOREIGN PATENT DOCUMENTS

| | | |
|---|---|---|
| EP | 0 990 650 A1 | 6/1998 |
| WO | WO 92/00338 | 1/1992 |
| WO | WO 94/03162 | 2/1994 |
| WO | WO 94/13275 | 6/1994 |
| WO | WO 97/35579 | 10/1997 |
| WO | WO 98/18458 | 5/1998 |
| WO | WO 98/31354 | 7/1998 |
| WO | WO 98/56768 | 12/1998 |
| WO | WO 00/12475 | 3/2000 |
| WO | WO 00/12510 | 3/2000 |
| WO | WO 00/16761 | 3/2000 |
| WO | WO 00/35922 | 6/2000 |
| WO | WO 00/44753 | 8/2000 |
| WO | WO 00/77002 | 12/2000 |
| WO | WO 00/77010 | 12/2000 |
| WO | WO 01/40183 | 6/2001 |
| WO | WO 01/70207 * | 9/2001 |
| WO | WO 01/70223 | 9/2001 |
| WO | WO 01/70230 | 9/2001 |
| WO | WO 01/83487 | 11/2001 |
| WO | WO 01/85152 | 11/2001 |
| WO | WO 02/40456 | 5/2002 |
| WO | WO 02/098350 | 12/2002 |
| WO | WO 02/098350 A2 * | 12/2002 |
| WO | WO 03/000663 | 1/2003 |
| WO | WO 03/051291 | 6/2003 |
| WO | WO 03/051352 | 6/2003 |
| WO | WO 2004/028451 | 4/2004 |

OTHER PUBLICATIONS

Chang et al., "Mechanism of the Ocular Hypotensive Action of Ketanserin," *J. of Ocular Pharmacology*, vol. 1(2), pp. 137-147 (1985).

Fiorella et al., "Role of 5-HT$_{2A}$ and 5-HT$_{2C}$ receptors in the stimulus effects of hallucinogenic drugss II: reassessment of LSD false positives," *Psychopharmacology*, vol. 121, pp. 357-362 (1995).

Grandolini et al., "92/New Heterocyclic Ring Systems from α-Hydroxymethyleneketones," *Gazzetta Chimica Italiana*, vol. 106, pp. 1083-1094 (1976).

Gupta et al., "Therapeutic Potentials of 5-HT Receptor Modulators," *Indian J. of Pharmacology*, vol. 26, pp. 94-107 (1994).

Johnson et al., "Binding to the Serotonin 5-Ht$_2$ Receptor by the Enantiomers of $^{125}$I-DO," *Neuropharmacology*, vol. 26(12), pp. 1803-1806 (1987).

Krootila et al., "Effect of Serotonin and Its Antagonist (Ketanserin) on Intraocular Pressure in the Rabbit," *J. of Ocular Pharmacology*, vol. 3(4), pp. 279-290 (1987).

Mallorga et al., "Characterization of Serotonin Receptors in the Iris + ciliary body of the albino rabbit," *Current Eye Research*, vol. 6(3), pp. 527-532 (1987).

Mano et al., "The Effect of Anplag (Sarpogelate HCL), New Selective 5-HT$_2$ Antagonist on Intraocular Pressure in Rabbits," *IOVS*, vol. 36(4), S719 (1995).

May et al., "A Novel and Selective 5-HT$_2$ Receptor Agonist with Ocular Hypotensive Activity: (S)-(+)-1-(2-Aminopropyl)-8,9-dihydropyrano[3,2-e]indole," *J. Med. Chem.*, vol. 46, pp. 4188-4195 (2003).

May et al., "Evaluation of the Ocular Hypotensive Response of Serotonin 5-HT$_{1A}$ and 5-HT$_2$ Receptor Ligands in Conscious Ocular Hypertensive Cynomolgus Monkeys," *J. of Pharmacology and Experimental Therapeutics*, vol. 306(1), pp. 301-309 (2003).

Osborne et al., "Do Beta-Adrenoceptors and Serotonin 5-HT$_1$A Receptors have Similar Functions in the control of Intraocular Pressure in the Rabbit?", *Ophthalmologica*, vol. 210, pp. 308-314 (1996).

Osborne et al., "5-Hydroxytryptamine$_{1A}$ agonists: potential use in glaucoma. Evidence from animal studies," *Eye*, vol. 14(38), pp. 454-463 (2000).

Portal et al., "The Synthesis of Benzo(b) Thieno and Benzo(b) Furo Indazole Derivatives. The Report of Three Novel Heterocyclic Systems," *Anales Asoc. Quim. Argentina*, vol. 59, pp. 69-76 (1971).

Sequeria et al., "Synthesis of Fused Indazole Derivatives," *Indian J. of Chemistry*, vol. 26B, pp. 436-439 (1987).

Shimada et al., "Synthesis and Structure-Activity Relationships of a Series of substituted 2-(1H-Furo[2,3-G]Indazol-1-yl)Ethylamine Derivatives as 5-HT2C Receptor Agonists," Poster MEDI348, ACS National Meeting Boston, Aug. 2002.

Shimada et al., "Synthesis and Structure-Activity Relationships of a Series of substituted 2-(1H-Furo[2,3-G]Indazol-1-yl)Ethylamine Derivatives as 5-HT2C Receptor Agonists," *Bioorganic & Medicinal Chemistry*, vol. 16, pp. 1966-1982 (2008).

Takenaka et al., "The Effect of Inplag. Novel Selective 5-HT2 Antagonist on Intraocular Pressure in Glaucoma Patients," IOVS, Vo. 36(4), S734 (1995).

Wang et al., "Effect of 5-methylurapidil, an $\alpha_{1a}$ adrenergic antagonist and 5-hydroxytryptamine$_{1a}$ agonist, on aqueous humor dynamics in monkeys and rabbits," *Current Eye Research*, vol. 16(8), pp. 769-775 (1997).

Wang et al., "Effect of $_p$MPPI Hydrochloride (p-MPPI) Applied before 5-methylurapidil (5-MU) on Intracular Pressure (IOP) in Normal Monkeys," *IOVS*, vol. 39(4) (1998) Abstract 2236-B93.

* cited by examiner

SUBSTITUTED FURO[2,3-G]INDAZOLES FOR THE TREATMENT OF GLAUCOMA

This application claims priority from U.S. Provisional Application, Ser. No. 60/525,635 filed Nov. 26, 2003.

BACKGROUND OF THE INVENTION

The present invention relates to the use of substituted furanoindazoles for lowering and controlling normal or elevated intraocular pressure (IOP) and for treating glaucoma.

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be at high risk for the eventual development of the visual loss associated with glaucoma. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

Serotonergic 5-$HT_{1A}$ agonists have been reported as being neuroprotective in animal models and many of these agents have been evaluated for the treatment of acute stroke among other indications. This class of compounds has been mentioned for the treatment of glaucoma (lowering and controlling IOP), see e.g., WO 98/18458 (DeSantis, et al.) and EP 0771563A2 (Mano, et al.). Osborne, et al. (Ophthalmologica, Vol. 210:308-314, 1996) teach that 8-hydroxydipropylaminotetralin (8-OH-DPAT) (a 5-$HT_{1A}$ agonist) reduces IOP in rabbits. Wang, et al. (Current Eye Research, Vol. 16(8):769-775, August 1997, and IVOS, Vol. 39(4), S488, March, 1998) indicate that 5-methylurapidil, an $\alpha_{1A}$ antagonist and 5-$HT_{1A}$ agonist lowers IOP in the monkey, but attribute the IOP effect to its $\alpha_{1A}$ receptor activity. Also, 5-$HT_{1A}$ antagonists are disclosed as being useful for the treatment of glaucoma (elevated IOP) (e.g., WO 92/0338, McLees). Furthermore, DeSai, et al. (WO 97/35579) and Macor, et al. (U.S. Pat. No. 5,578,612) relate to the use of 5-$HT_1$ and 5-$HT_{1-like}$ agonists for the treatment of glaucoma (elevated IOP). These anti-migraine compounds, e.g., sumatriptan and naratriptan and related compounds, are 5-$HT_{1B,D,E,F}$ agonists.

It has been found that serotonergic compounds which possess agonist activity at 5-$HT_2$ receptors effectively lower and control normal and elevated IOP and are useful for treating glaucoma, see commonly owned co-pending application, U.S. patent application Ser. No. 09/787,332 corresponding to WO 00/16761, both of which are incorporated in their entirety by reference herein. Compounds that act as agonists at 5-$HT_2$ receptors are well known and have shown a variety of utilities, primarily for disorders or conditions associated with the central nervous system (CNS). U.S. Pat. No. 5,494,928 relates to certain 2-(indol-1-yl)-ethylamine derivatives that are 5-$HT_{2C}$ agonists for the treatment of obsessive compulsive disorder and other CNS derived personality disorders. U.S. Pat. No. 5,571,833 relates to tryptamine derivatives that are 5-$HT_2$ agonists for the treatment of portal hypertension and migraine. U.S. Pat. No. 5,874,477 relates to a method for treating malaria using 5-$HT_{2A/2C}$ agonists. U.S. Pat. No. 5,902,815 relates to the use of 5-$HT_{2A}$ agonists to prevent adverse effects of NMDA receptor hypo-function. WO 98/31354 relates to 5-$HT_{2B}$ agonists for the treatment of depression and other CNS conditions. WO 00/12475 relates to indoline derivatives, and WO 00/12510 and WO 00/44753 relate to certain indole derivatives as 5-$HT_{2B}$ and 5-$HT_{2C}$ receptor agonists for the treatment of a variety of disorders of the central nervous system, but especially for the treatment of obesity. WO 00/35922 relates to certain pyrazino[1,2-a]quinoxaline derivates as 5-$HT_{2C}$ agonists for the treatment of obsessive compulsive disorder, depression, eating disorders, and other disorders involving the CNS. WO 00/77002 and WO 00/77010 relate to certain substituted tetracyclic pyrido [4,3-b]indoles as 5-$HT_{2C}$ agonists with utility for the treatment of central nervous system disorders including obesity, anxiety, depression, sleep disorders, cephalic pain, and social phobias among others. WO 02/40456 and WO 03/00663 relate to certain substituted 1-(pyrazinyl)-piperazines and substituted 1-(pyrimidinyl)-piperazines, respectively, as agonists or antagonists at 5-$HT_{2C}$ receptors for the treatment of a variety of central nervous system related disorders, especially obesity and sexual dysfunction. Agonist response at the 5-$HT_{2A}$ receptor is reported to be the primary activity responsible for hallucinogenic activity, with some lesser involvement of the 5-$HT_{2C}$ receptor possible [Psychopharmacology, Vol. 121:357, 1995].

Few furan or pyran containing fused indazoles have been reported. The chemical synthesis of 7-methyl- and 1,7-dimethyl-1H-furo[2,3-g]indazole [*Gazz. Chim Ital.* 106, 1083 (1976)] as well as that of 3-methyl- and 1-(4-aminophenyl)-3-methyl-1H-benzo[b]furo[2,3-g]indazole [*An. Asoc. Quim. Argent.* 59, 69 (1971)] has been reported without discussion of their utility. European Patent Application EP 990,650 (Intnl. Publication Number WO 98/56768) relates to substituted 2-(furo[2,3-g]indazol-1-yl)-ethylamines, such as (S)-2-(furo[2,3-g]indazol-1-yl)-1-methylethylamine, which are reported to have high selectivity and affinity for 5-$HT_{2C}$ receptors and are potentially useful for treating a variety of central nervous system disorders. The chemical synthesis of 9-methyl-1H-pyrano[2,3-g]indazol-7-one and the corresponding non-methylated compound was reported [*Indian J. Chem.* 26B, 436 (1987)] with no mention of utility.

U.S. Pat. Nos. 5,561,150 and 5,646,173 relate to certain tricyclic pyrazole derivative compounds which are identified as being 5-$HT_{2C}$ agonists for the treatment of CNS diseases and are primarily directed to lipophilic analogs that have a high probability of entering the brain. Similarly, WO 98/56768 relates to tricyclic 5-$HT_{2C}$ agonists for the treatment of CNS diseases. All the patents and publications mentioned above and throughout are incorporated in their entirety by reference herein.

5-Hyroxytyptamine (serotonin) does not cross the blood-brain barrier and enter the brain. However, in order to increase brain serotonin levels the administration of 5-hydroxy-tryptophan can be employed. The transport of 5-hydroxy-tryptophan into the brain readily occurs, and once in the brain 5-hydroxy-tryptophan is rapidly decarboxylated to provide serotonin.

Accordingly, there is a need to provide new compounds which avoid the disadvantages described above and which provide increased chemical stability and a desired length of therapeutic activity, for instance, in decreasing intraocular pressure and treating glaucoma.

SUMMARY OF THE PRESENT INVENTION

A feature of the present invention is to provide novel compounds which are 5-HT$_2$ agonists.

Another feature of the present invention is to provide compounds which have increased chemical stability and which are useful in lowering and controlling normal or elevated intraocular pressure and/or treating glaucoma.

Another feature of the present invention is to provide compounds which provide a desired level of therapeutic activity in lowering and controlling normal or elevated intraocular pressure and/or treating glaucoma.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a compound having the Formula A:

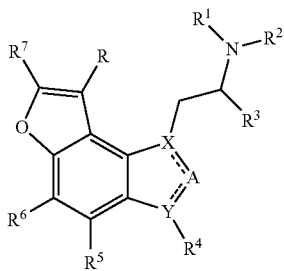

and described more fully below.

The present invention further relates to pharmaceutical compositions containing at least one compound of Formula A.

The present invention further relates to methods to lower and/or control normal or elevated intraocular pressure by administering an effective amount of a composition containing a compound having Formula A as described above.

The present invention also relates to a method for treating glaucoma which involves administering an effective amount of a composition containing a compound having Formula I as described above.

It is to be understood that both the foregoing general description and the following detailed description are exemplary and explanatory only and are intended to provide a further explanation of the present invention, as claimed.

DETAILED DESCRIPTION OF THE PRESENT INVENTION

The present invention relates to a variety of compounds which are useful according to the present invention. These compounds are represented by the following Formula A.

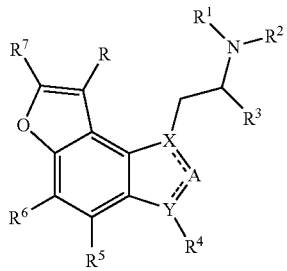

Wherein R, $R^1$ and $R^2$ are independently chosen from hydrogen, $C_{1-4}$alkyl;

$R^3$ is selected from hydrogen, $C_{1-4}$alkyl, or $R^2$ and $R^3$ can complete a pyrrolidine or piperidine ring, which can be substituted with $C_{1-4}$alkyl;

$R^4$ is hydrogen, halogen, $C_{1-4}$alkyl;

$R^5$ and $R^6$ are independently chosen from hydrogen, halogen, $C_{1-6}$alkyl, $C_{1-6}$alkylthio, $C_{1-6}$alkylsulfonyl, $C_{1-6}$alkylsulfoxide, nitrile, $C_{1-6}$alkyl substituted with halogen;

$R^7$ is chosen from C=OR$^9$; S(O)$_m$R$^{10}$; NR$^1$—(C=O)—R$^{11}$; $C_{1-6}$alkyl substituted with hydroxyl, $C_{1-6}$alkoxy, OC(=O) $C_{1-8}$, $CO_2H$, $CO_2C_{1-6}$alkyl, C(=O)NR$^{12}$R$^{13}$, S(O)$_m$NR$^{12}$R$^{13}$, NR$^{14}$R$^{15}$, phenyl or a saturated or unsaturated 5 or 6-membered heterocyclic ring which can contain 1-4 heteroatoms selected from N, O, or S and can be unsubstituted or substituted with $C_{1-6}$alkyl, $C_{1-6}$alkoxy, halogen, haloC$_{1-4}$alkyl, phenyl or pyridinyl; or $R^7$ can be chosen from a heterocyclic ring selected from an oxazole such as oxazol-2-yl, 4,5-dihydro-oxazol-2-yl, or benzoxazol-2-yl, an oxazine such as 5,6-dihydro-[1,3]oxazin-2-yl, a thiazole such as thiazol-2-yl, 4,5-dihydro-thiazol-2-yl, or benzothiazol-2-yl, an imidazole such as imidazol-2-yl, or imidazolidin-2-yl, [1,2,4]oxadiazol-5-yl, [1,2,4]oxadiazol-3-yl, [1,2,4]thiadiazol-5-yl, or [1,2,4]thiadiazol-3-yl which can be unsubstituted or substituted with $C_{1-6}$alkyl, $C_{1-6}$alkoxy, phenyl or pyridinyl, or $C_{1-6}$alkyl substituted with phenyl or pyridinyl;

but $R^7$ cannot be hydrogen, lower alkyl, hydroxyl, lower alkoxy, amino, mono- or di-loweralkyl amino, lower alkanoylamino, or halogen;

$R^8$ is selected from $C_{1-6}$alkyl, phenyl which can be substituted with $C_{1-6}$alkyl, $C_{1-6}$alkoxy, NR$^1$(C=O)C$_{1-6}$alkyl, or halogen;

$R^9$ is chosen from hydroxyl; $C_{1-6}$alkoxy; $C_{1-6}$alkoxy substituted with phenyl or pyridinyl which can be substituted with $C_{1-4}$alkoxy or halogen; NR$^{16}$R$^{17}$; $C_{1-6}$alkyl; or $C_{1-6}$alkyl substituted with hydroxyl, $C_{1-6}$alkoxy, NR$^{12}$R$^{13}$, $CO_2H$, $CO_2C_{1-6}$alkyl, S(O)$_m$NR$^{12}$R$^{13}$, halogen, or phenyl or a heterocyclic ring selected from pyrrolidinyl, imidazoyl, morpholinyl, oxazolyl, isoxazolyl, thiazolyl, or tetrazolyl, or pyridinyl which can be unsubstituted or substituted with $C_{1-6}$alkyl, $C_{1-6}$alkoxy, halogen, haloC$_{1-4}$alkyl;

$R^{10}$ is chosen from NR$^{12}$R$^{13}$; $C_{1-6}$alkyl; CH$_2$phenyl or CH$_2$pyridinyl which can be substituted with $C_{1-6}$alkyl, $C_{1-6}$alkoxy, halogen, or haloC$_{1-4}$alkyl; or $C_{2-6}$alkyl substituted with hydroxyl, $C_{1-6}$alkoxy, NR$^{12}$R$^{13}$, $CO_2H$, $CO_2C_{1-6}$ alkyl, phenyl, pyridinyl or imidazolyl which can be substituted with $C_{1-6}$alkyl, $C_{1-6}$alkoxy, halogen, haloC$_{1-4}$ alkyl;

$R^{11}$ is NH$_2$; NR$^1$R$^2$; $C_{1-6}$alkyl substituted with hydroxyl, $C_{1-6}$alkoxy, $CO_2H$, $CO_2C_{1-6}$alkyl, phenyl or a saturated or unsaturated 5 or 6-membered heterocyclic ring which can contain 1-4 heteroatoms selected from N, O, or S and can be unsubstituted or substituted with $C_{1-6}$alkyl, $C_{1-6}$alkoxy, halogen, halo$C_{1-4}$alkyl;

$R^{12}$ and $R^{13}$ are independently selected from hydrogen; $C_{1-6}$alkyl; $CH_2Z$, where Z is selected from phenyl, pyridinyl, furanyl, thiophenyl, pyrimidinyl, pyrazinyl, or pyridazinyl, and which can be substituted with $C_{1-6}$alkyl, $C_{1-6}$alkoxy, halogen, or halo$C_{1-4}$alkyl; $C_{2-6}$alkyl substituted with hydroxyl, $C_{1-6}$alkoxy, $CO_2H$, $CO_2C_{1-6}$alkyl, $NR^1COC_{1-6}$alkyl, or halogen; or $R^{12}$, $R^{13}$, and the intervening nitrogen atom can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with $C_{1-4}$alkyl or $C_{1-4}$alkyl substituted with hydroxy, $C_{1-4}$alkoxy or halogen;

$R^{14}$ and $R^{15}$ are independently selected from hydrogen, $C_{1-6}$alkyl, hydroxyl, $C_{1-6}$alkoxy, (C=O)—$R^{11}$, $S(O)_mR^8$, phenyl or pyridinyl which can be substituted with $C_{1-6}$alkyl, $C_{1-6}$alkoxy, halogen, or halo$C_{1-4}$alkyl; or $R^{14}$, $R^{15}$ and the nitrogen atom to which they are attached can form a heterocyclic ring selected from pyrrolidine, piperazine, or piperidine, which can be substituted with $C_{1-6}$alkyl, phenyl, or pyridinyl;

$R^{16}$ and $R^{17}$ are independently selected from hydrogen; $C_{1-6}$alkyl; hydroxyl; $C_{1-6}$alkoxy; $CH_2Z$, where Z is selected from phenyl, pyridinyl, furanyl, thiophenyl, pyrimidinyl, pyrazinyl, or pyridazinyl, and which can be substituted with $C_{1-6}$alkyl, $C_{1-6}$alkoxy, halogen, or halo$C_{1-4}$alkyl; $C_{2-6}$alkyl substituted with hydroxyl, $C_{1-6}$alkoxy, halogen, $NR^1(C=O)C_{1-6}$alkyl, or a phenyl or a heterocyclic ring selected from a pyrrole, such as pyrrolidin-2-yl, an imidazole such as imidazo-2-yl or imidazo-4-yl, a morpholine such as morpholin-3-yl, a piperidine such as piperidin-4-yl, oxazolyl, isoxazolyl, thiazolyl, tetrazolyl, pyridinyl, which can be unsubstituted or substituted with $C_{1-6}$alkyl, $C_{1-6}$alkoxy, halogen, halo$C_{1-4}$alkyl, phenyl$C_{1-4}$alkyl, oxo (=O); or $R^{16}$, $R^{17}$, and the intervening nitrogen atom can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with $C_{1-4}$alkyl or $C_{1-4}$alkyl substituted with hydroxy, oxo (=O), $C_{1-4}$alkoxy, or phenyl;

m is 0-2;

A is N or CH; and

X and Y are either N or C, wherein X and Y cannot be the same; and the dashed bonds denote a suitably appointed single and double bond.

In the above definitions, the total number of carbon atoms in a substituent group is indicated by the $C_{i-j}$ prefix where the numbers i and j define the number of carbon atoms. This definition includes straight chain, branched chain, and cyclic allyl or (cyclic alkyl)alkyl groups. A substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

Synthesis

Compounds of Formula A can be prepared by using one of several synthetic procedures. For example, esters of 1-(2-aminopropyl)-1H-furo[2,3-g]indazole-7-carboxylic acid can be prepared from an appropriately protected 1-(2-aminopropyl)-1H-furo[2,3-g]indazol-6-ol (1) either via the dihydrofuran intermediate 4 [Helv. Chim. Acta, 84:2198 (2001)] or by way of the 7-formyl intermediate 3 as outlined in Scheme 1. As used herein, Pg denotes a suitable protective group to assure that a particular atom is not modified during the indicated chemical reaction. See, for example, the use of carbobenzyloxy in the Examples below.

Scheme 1

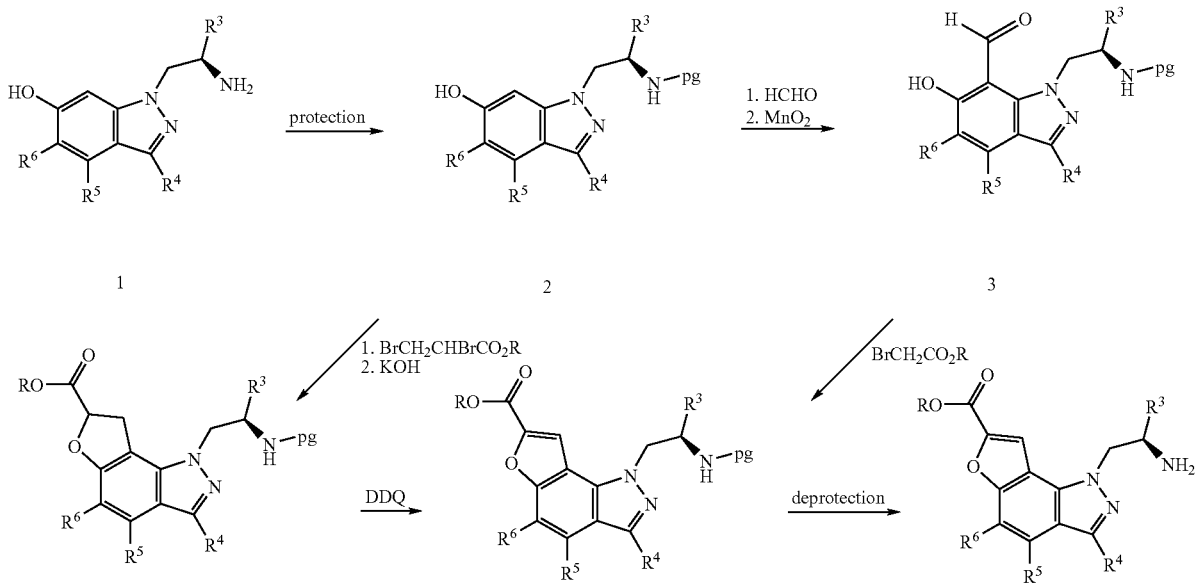

As described below, other compounds of Formula A can be prepared from the appropriately N-protected ester intermediates 5 through select functional group transformations well-known in the art. For example, reaction of certain esters 5 with the desired primary or secondary amine or ammonia followed by deprotection will provide the desired 7-carboxamide compounds 7 of Formula A. Alternatively, it may be preferable to initially hydrolyze an ester 5 to the corresponding carboxylic acid 8, which can be suitably activated, to such as with an appropriated carbodiimide reagent, and then reacted with the desired amine to give, after deprotection, the desired 7-carboxamides. Yet other compounds of Formula A can be prepared by initially reducing the intermediate ester or acid to the corresponding 7-hydroxymethyl intermediate 9, which can subsequently be activated, such as by formation of an appropriate sulfonate ester, followed by reaction with a desirable nucleophile and suitable deprotection as outlined in Scheme 2.

Scheme 2:

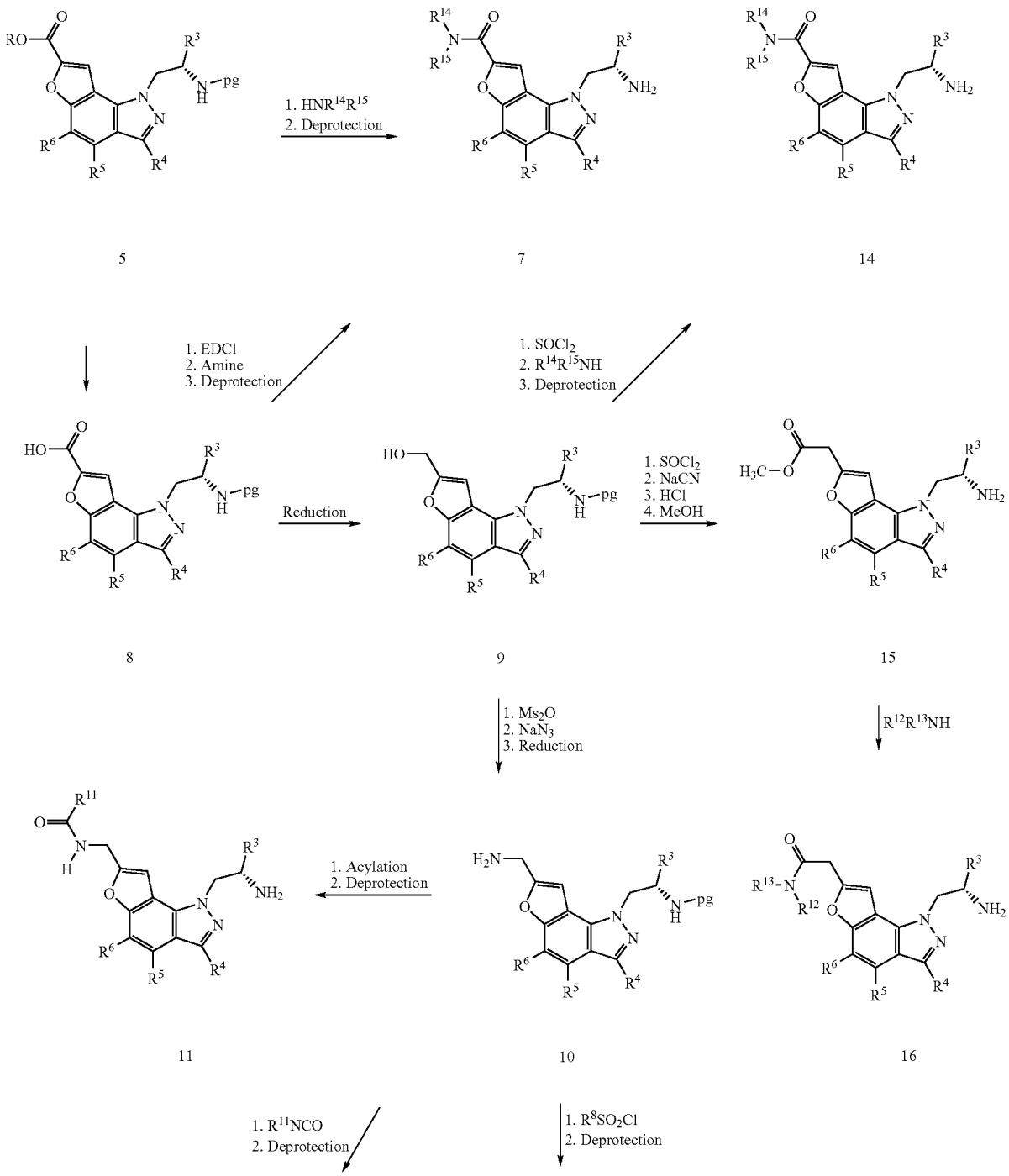

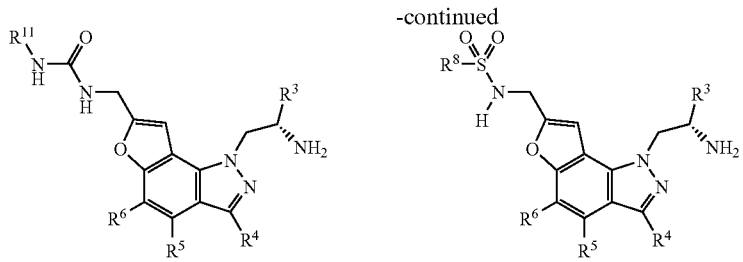

12

13

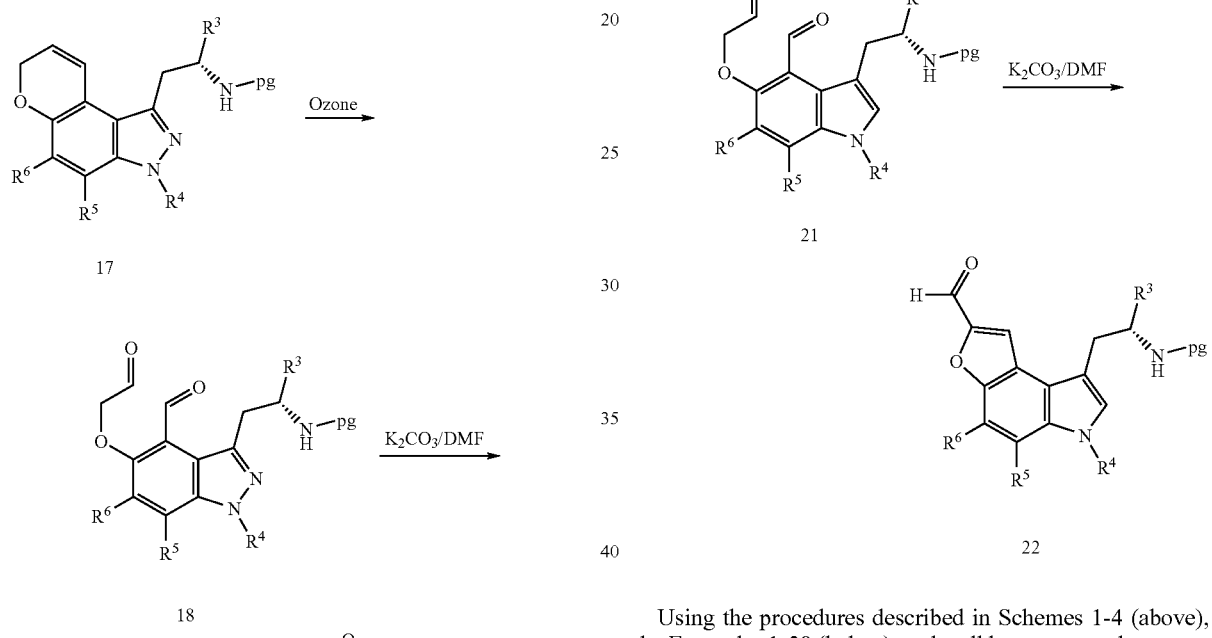

Scheme 3

17

18

19

Scheme 4

20

21

22

Using the procedures described in Schemes 1-4 (above), the Examples 1-20 (below), and well known procedures, one skilled in the art can prepare the compounds disclosed herein.

The following examples are given to illustrate the preparation of compounds that are the subject of this invention but should not be construed as implying any limitations to the claims. The preparation of preferred compounds of Formula A is described in Examples 3, 4, 10 and 11, with Examples 4 and 11 describing the preparation of the most preferred compounds. The proton magnetic resonance spectrum of each compound of the Examples was consistent with the assigned structure.

EXAMPLE 1

1-((S)-2-Aminopropyl)-1H-furo[2,3-g]indazole-7-carboxylic acid ethyl ester fumarate Step A: [(S)-2-(6-Hydroxy-indazol-1-yl)-1-methyl-ethyl]-carbamic acid benzyl ester 1-((S)-2-Aminopropyl)-1H-indazol-6-ol [prepared in accordance with commonly owned WO 02/098862A1, the contents of which are by this reference incorporated herein] (2.00 g, 10.5 mmol) was suspended in THF (20 mL) and saturated aqueous sodium bicarbonate (10 mL) and benzyl chloroformate (1.50 mL, 15 mol) were added. The mixture was stirred at room temperature until the starting amine dissolved. Saturated aqueous sodium bicarbonate (150 mL) was added and the reaction mixture extracted with ethyl acetate (3×150 mL). The combined organic layers were dried (magnesium sulfate), filtered, and evaporated to give a tan foam (2.65 g, 78%) which was pure by LC/MS (+APCI) m/z 326 (M+H$^+$).

Step B: [(S)-2-(6-Hydroxy-7-hydroxymethyl-indazol-1-yl)-1-methylethyl]-carbamic acid benzyl ester To a stirred solution of the product from Step A (2.2 g, 6.8 mol) in THF (30 mL) was added potassium hydroxide (3.3%, 5 mL) and aqeous formaldehyde (37%, 1.6 mL); this solution was heated at 55° C. for 2 h followed by stirring for an additional 18 h at room temperature. A saturated ammonium chloride solution (30 mL) was added to the reaction mixture, which was extracted with ethyl acetate (3×50 mL). The combined extracts were washed with brine (30 mL), dried and evaporated. The residue was purified by chromatography (silica, 50% ethyl acetate in hexane) to give 6 as an oil (2.2 g, 91%): $^1$H NMR δ (DMSO-d$_6$) δ 7.87 (s, 1H), 7.46 (d, 1H, J=8.5 Hz), 7.32 (m, 5H), 6.78 (d, 1H, J=8.5 Hz), 6.50 (d, 1H, J=7.8 Hz), 4.78 (s, 2H), 4.68-4.48 (m), 1.03 (d, 3H, J=6.0 Hz); MS (ES) m/z 356 (M$^+$).

Step C: [(S)-2-(7-Formyl-6-hydroxy-indazol-1-yl)-1-methylethyl]-carbamic acid benzyl ester To a stirred solution of the product from Step B (0.75 g, 2.11 mmol) in tetrahydrofuran (10 mL) was added activated manganese dioxide (0.75 g) and the resultant solution was stirred for 18 h at 45° C. The solution was filtered through a filter aide and the filtrate was evaporated. The residue was purified by chromatography (silica, 30% ethyl acetate in hexane) to yield a solid (0.54, 72%): mp 135-137° C.; MS (ES) m/z 254 (M$^+$); $^1$H NMR (CDCl$_3$) δ 13.18 (s, 1H), 10.77 (s, 1H), 7.90 (s, 1H), 7.57 (d, 1H, J=8.0 Hz), 7.33-7.27 (m, 5H), 6.81 (d, 1H, J=8.0 Hz), 5.05 (m, 3H), 4.70 (m, 1H), 4.52-4.47 (m, 1H), 4.23-4.19 (m, 1H), 1.22 (d, 3H, J=8.0 Hz).

Step D: 1-((S)-2-Benzyloxycarbonylaminopropyl)-1H-furo[2,3-g]indazole-7-carboxylic acid ethyl ester To a stirred solution of the product from Step C (0.20 g, 0.56 mmol) in DMF (10 mL) was added potassium carbonate (0.23 g, 1.68 mmol) followed by ethyl 2-bromoacetate (0.07 mL, 0.62 mmol) at room temperature and the resultant solution was heated at 70° C. for 20 h. Saturated aqueous ammonium chloride (20 mL) was added followed by ethyl acetate (50 mL). The organic layer was separated and the aqueous was extracted with ethyl acetate (3×50 mL). The combined organic layers were washed with brine (30 mL), dried and evaporated. The residue was purified by chromatography (silica, 50% ethyl acetate in hexane) to give an oil (0.10 g, 42%): MS(ES) m/z 422 (M$^+$); $^1$H NMR (CDCl$_3$) δ 8.17 (s, 1H), 8.05 (s, 1H), 7.72 (d, 1H, J=8.8 Hz), 7.43 (d, 1H, J=8.8 Hz), 7.33 (m, 5H), 5.05-5.09 (m, 2H), 4.58 (m, 1H), 4.30 (m, 2H), 1.45 (t, 3H, J=7.2 Hz), 1.17 (d, 3H, J=6.8 Hz).

Step E: 1-((S)-2-Aminopropyl)-1H-furo[2,3-g]indazole-7-carboxylic acid ethyl ester fumarate To a solution of the product from Step D (0.10 g, 0.24 mmol) in ethanol (5 mL) under nitrogen was added Pd/C (10%, 0.01 g) and the suspension was stirred under a hydrogen atmosphere at room temperature for 18 h. The solution was filtered through a filter aide and the filtrate was concentrated to a residue, which was purified by chromatography (silica, dichloromethane, 10% methanol in dichloromethane and 15% methanol in dichloromethane) to give a syrup (0.06 g, 88%). The syrup was dissolved in methanol and combined with a solution of fumaric acid (0.02 g) in methanol (1.0 mL). Evaporation of this mixture provided a residue that solidified from a mixture of methanol and ethyl acetate (0.06 g): mp 184-185° C.; MS (ES) m/z 288 (M$^+$); $^1$H NMR (DMSO-d$_6$) δ 8.46 (s, 1H), 8.28 (s, 1H), 7.93 (d, 1H, J=8.8 Hz), 7.55 (d, 1H, J=8.8 Hz,), 6.55 (s, 3H), 4.84-4.89 (m, 2H), 4.42 (q, 2H, J=7.2 Hz), 3.72 (m, 1H), 1.37 (t, 7H, J=7.2 Hz), 1.14 (d, 3H, J=6.4 Hz); Analysis. Calculated for $C_{15}H_{17}N_3O_3 \cdot 1.5\ C_4H_4O_4 \cdot 1.1\ H_2O$: C, 52.41; H, 5.28; N, 8.73. Found: C, 52.18; H, 5.27; N, 9.12.

EXAMPLE 2

[1-((S)-2-Aminopropyl)-1H-furo[2,3-g]indazol-7-yl]-methanol

Step A: 1-((S)-2-Benzyloxycarbonylaminopropyl)-1H-furo[2,3-g]indazole-7-carboxylic acid benzyl ester To a stirred solution of the product from Step C, Example 1 (0.12 g, 0.32 mmol) in DMF (10 mL) was added potassium carbonate (0.15 g, 1.05 mmol) followed by benzyl 2-bromoacetate (0.08 g, 0.48 mmol) at room temperature and the mixture was heated at 70° C. for 20 h. A saturated aqueous solution of ammonium chloride (20 mL) was added followed by ethyl acetate (50 mL). The organic layer was separated and the aqueous was extracted with ethyl acetate (3×50 mL). The combined organic layers were washed with brine (30 mL), dried and evaporated to a residue, which was purified by chromatography (silica, 50% ethyl acetate in hexane) to give a solid (0.11 g, 71%): mp 140-141° C.; MS (ES) m/z 484 (M$^+$).

Step B: [(S)-2-(7-Hydroxymethyl-furo[2,3-g]indazol-1-yl)-1-methylethyl]-carbamic acid benzyl ester To a stirred solution of the product from Step A (0.13 g, 0.27 mmol) in ethanol (10 mL) was added calcium chloride (0.06 g, 0.54 mmol) in THF (2 mL) followed by sodium borohydride (0.04 g, 1.07 mmol) at 0° C. and the mixture was stirred at room temperature for 20 h. The reaction mixture was evaporated to a residue and a saturated aqueous solution of ammonium chloride (20 mL was added followed by ethyl acetate (50 mL). The organic layer was separated and the aqueous was extracted with ethyl acetate (3×50 mL). The combined organic layers were washed with brine (30 mL), dried and evaporated to a residue, which was purified by chromatography (silica, 50% ethyl acetate in hexane) to give an oil (0.05 g, 49%); MS (ES) m/z 380 (M$^+$).

Step C: [1-((S)-2-Aminopropyl)-1H-furo[2,3-g]indazol-7-yl]-methanol

A solution of the product from Step B (0.05 g, 0.13 mmol) in ethanol (5 mL) was treated as described in Step E of Example 1, but using a mixture of 9% methanol:1% ammonium hydroxide in dichloromethane as chromatography solvent to give the free base as an amorphous solid (0.032 g): mp 110-112° C.; MS (ES) m/z 246 (M$^+$); $^1$H NMR (DMSO-d$_6$) δ

8.16 (s, 1H), 7.62 (d, 1H, J=9.2 Hz), 7.41 (d, 1H, J=9.2 Hz), 6.49 (s, 1.7H), 4.65 (m, 3H), 4.55 (m, 1H), 3.53 (m, 1H), 1.03 (d, 3H, J=6.4 Hz). Analysis. Calculated for $C_{13}H_{18}N_3O_2$: C, 62.29; H, 6.27; N, 16.76. Found: C, 62.25; H, 6.09; N, 16.73.

EXAMPLE 3

1-((S)-2-Aminopropyl)-1H-furo[2,3-g]indazole-7-carboxylic acid amide

Step A: 1-((S)-2-Benzyloxycarbonylaminopropyl)-1H-furo[2,3-g]indazole-7-carboxylic acid To a solution of the product of Step A, Example 2 (0.15 g, 0.31 mmol) in ethanol (10 mL) was added lithium hydroxide (0.026 g, 0.62 mmol) in water (1 mL) and stirred at room temperature for 16 h. The reaction mixture was evaporated to a residue and a saturated aqueous solution of ammonium chloride (20 mL) was added followed by the addition of phosphoric acid (1 M) until the solution was neutral. The mixture was extracted with ethyl acetate (3×50 mL) and the combined extracts were washed with brine (30 mL), dried and evaporated. The residue was purified by chromatography (silica, dichloromethane, 5% methanol in dichloromethane, 10% methanol in dichloromethane) to give an oil (0.12 g, 98%): MS (ES) m/z 394 (M+); $^1$H NMR (CD$_3$OD) δ 7.91 (s, 1H), 7.81 (s, 1H), 7.58 (d, 1H, J=8.8 Hz), 7.25 (d, 1H, J=8.8 Hz), 7.14-7.02 (m, 5H), 4.81 (s, 2H), 4.49-4.42 (m, 2H), 4.17 (m, 1H), 1.18 (d, 3H, J=6.8 Hz).

Step B: [(S)-2-(7-Carbamoyl-furo[2,3-g]indazol-1-yl)-1-methylethyl]-carbamic acid benzyl ester To a stirred solution of the product from Step A (0.17 g, 0.43 mmol) in DMF (5 mL) was added 1-hydroxy-benzotriazole hydrate (0.029 g, 0.21 mmol) and 1-(3-dimethylaminopropyl)-3-ethylcarbodiimide hydrochloride (0.13 g, 0.65 mmol) followed by a solution of ammonia in dioxane (0.5 M, 1.72 mL, 0.86 mmol). After 18 h, a saturated aqueous solution of ammonium chloride (20 mL) added and the mixture was extracted with ethyl acetate (3×50 mL). The combined extracts were washed with brine, dried and evaporated. The residue was purified by chromatography (silica, dichloromethane, 5% methanol in dichloromethane) to give an oil (0.14 g, 83%): MS (ES) m/z 393 (M+); $^1$H NMR (CDCl$_3$) δ 8.20 (brs, 1H), 8.04 (s, 1H), 8.01 (s, 1H), 7.69 (d, 1H, J=8.0 Hz), 7.32-7.23 (m, 6H), 6.76 (brs, 2H), 5.03 (m, 2H), 4.63 (m, 2H), 4.40 (m, 1H), 1.16 (d, 3H, J=8.0 Hz).

Step C: 1-((S)-2-Aminopropyl)-1H-furo[2,3-g]indazole-7-carboxylic acid amide

A solution of the product from Step B (0.098 g, 0.25 mmol) in ethanol (10 mL) was treated as described in Step E of Example 1, but without chromatoghraphy, to give the fumarate salt (0.065 g): mp 170-172° C.; MS (ES) m/z 259 (M+); $^1$H NMR (DMSO-d$_6$) δ 8.29 (s, 1H), 8.21 (s, 1H), 7.83 (d, 1H, J=8.8 Hz), 7.67 (brs, 1H), 7.47 (d, 1H, J=8.8 Hz), 6.48 (s, 1H), 4.71-4.54 (m, 2H), 3.54 (m, 1H), 1.06 (d, 3H, J=6.4 Hz). Analysis. Calculated for $C_{13}H_{14}N_4O_2 \cdot 1.0 \, C_4H_4O_4 \cdot 0.2 \, H_2O$. C, 54.02; H, 4.91; N, 14.82. Found: C, 54.06; H, 5.25; N, 15.09.

EXAMPLE 4

1-((S)-2-Aminopropyl)-1H-furo[2,3-g]indazole-7-carboxylic acid methyl amide fumarate This compound was prepared by following a procedure similar to that described in Example 3, but replacing ammonia in dioxane with methylamine hydrochloride in Step B to give the fumarate salt: mp 180-182° C.; MS (ES) m/z 273 (M+); $^1$H NMR (DMSO-d$_6$) δ 8.75 (q, 1H, J=4.4 Hz), 8.21 (s, 1H), 8.19 (s, 1H), 7.82 (d, 1H J=8.8 Hz), 7.45 (d, 1H, J=8.8 Hz), 6.48 (s, 1H), 4.66-4.50 (m, 2H), 3.54 (m, 1H), 2.85 (d, 3H, J=4.4 Hz), 1.04 (d, 3H, J=6.4 Hz). Analysis. Calculated for $C_{14}H_{16}N_4O_2 \cdot 0.5 \, C_4H_4O_4 \cdot 1.0 \, H_2O$: C, 55.17; H, 5.79; N, 16.08. Found: C, 54.86; H, 5.71; N, 15.69.

EXAMPLE 5

1-((S)-2-Aminopropyl)-1H-furo[2,3-g]indazole-7-carboxylic acid (2-hydroxyethyl)-amide fumarate Step A: [(S)-2-[7-(2-Hydroxyethylcarbamoyl)-furo[2,3-g]indazol-1-yl]-1-methylethyl]-carbamic acid benzyl ester A stirred solution of the product from Step A, Example 2 (0.44 g, 0.91 mmol) in ethanolamine was heated at 80° C. for 8 h. A saturated aqueous solution of ammonium chloride (20 mL) was added and the mixture was extracted with ethyl acetate (3×50 mL). The combined extracts were washed with brine, dried and evaporated to a residue, which was purified by chromatography (silica, 60% ethyl acetate in hexane) to give an oil (0.23 g, 57%): MS (ES) m/z 437 (M+); $^1$H NMR (CDCl$_3$) δ 8.00 (s, 1H), 7.69 (d, 1H, J=8.0 Hz), 7.22-7.30 (m, 7H), 5.30 (brs, 1H), 5.03 (m, 2H), 4.63 (m, 1H), 4.40 (m, 1H), 4.15 (m, 1H), 3.85 (m, 2H), 3.65 (m, 2H), 1.26 (d, 3H, J=8.0 Hz).

Step B: 1-((S)-2-Aminopropyl)-1H-furo[2,3-g]indazole-7-carboxylic acid (2-hydroxyethyl)-amide A solution of the product from Step A (0.23 g, 0.52 mmol) in ethanol (10 mL) was treated as described in Step C of Example 3 to give the fumarate salt as an amorphous solid (0.14 g): MS (ES) m/z 303 (M+); $^1$H NMR (DMSO-d$_6$) δ 8.78 (t, 1H, J=6.6 Hz), 8.29 (s, 1H), 8.23 (1H), 7.83 (d, 1H, J=8.8 Hz), 7.47 (d, 1H J=8.8 Hz), 6.49 (s, 1H), 4.70-4.74 (m, 2H), 3.54-3.61 (m, 3H), 3.37-3.41 (m, 2H), 1.06 (d, 3H, J=6.6 Hz). Analysis. Calculated for $C_{15}H_{18}N_4O_3 \cdot 1.0 \, C_4H_4O_4 \cdot 1.75 \, H_2O$: C, 50.72; H, 5.71; N, 12.45. Found: C, 50.37; H, 5.68; N, 12.85.

EXAMPLE 6

1-((S)-2-Aminopropyl)-1H-furo[2,3-g]indazole-7-carboxylic acid [2-(3H-imidazol-4-yl)-ethyl]-amide fumarate This compound was prepared by following a procedure similar to that described in Example 5, but replacing ethanolamine in Step A with histamine to give the fumarate salt: mp 201-203° C.; MS (ES) m/z 353 (M+); $^1$H NMR (DMSO-d$_6$) δ 8.95 (t, 1H, J=6.6 Hz), 8.29 (s, 1H), 8.24 (s, 1H), 7.84 (d, 1H, J=8.8 Hz), 7.56 (s, 1H), 7.48 (d, 1H, J=8.8 Hz), 6.86 (s, 1H), 6.52 (s, 2H), 4.65-4.76 (m, 2H), 3.58 (m, 1H), 3.53-3.56 (m, 2H), 2.81 (t, 2H, J=7.2 Hz), 1.08 (d, 3H, J=6.4 Hz). Analysis.

Calculated for $C_{18}H_{20}N_6O_2 \cdot 1.3\ C_4H_4O_4 \cdot 1.3\ H_2O$: C, 52.90; H, 5.32; N, 15.96. Found: C, 52.65; H, 5.33; N, 16.19.

EXAMPLE 7

1-((S)-2-Aminopropyl)-1H-furo[2,3-g]indazole-7-carboxylic acid (2-morpholin-4-yl-ethyl)-amide This compound was prepared by following a procedure similar to that described in Example 5, but replacing ethanolamine in Step A with 4-(2-aminoethyl)morpholine to give the fumarate salt as an amorphous solid: MS (ES) m/z 373 (M$^+$); $^1$H NMR (DMSO-d$_6$) δ 8.81 (t, 1H J=6.6 Hz), 8.34 (s, 1H), 8.24 (s, 1H), 7.99 (d, 1H J=8.8 Hz), 7.51 (d, 1H, J=8.8 Hz), 6.55 (s, 4H), 4.65-4.84 (m, 2H), 3.58 (m, 1H), 3.53-3.56 (m, 5H), 3.45 (m, 2H), 1.06 (d, 3H, J=6.4 Hz).

EXAMPLE 8

1-((S)-2-Aminopropyl)-1H-furo[2,3-g]indazole-7-carboxylic acid (2-methoxyethyl)-amide This compound was prepared by following a procedure similar to that described in Example 5, but replacing ethanolamine in Step A with 2-methoxyethylamine to give, after deprotection, the fumarate salt: mp 75-76° C.; MS (ES) m/z 276 (M$^+$); $^1$H NMR (DMSO-d$_6$), δ 10.5 (1H, brs), 8.92 (1H, t, J=5.2 Hz), 8.41 (1H, s), 8.31 (1H, s), 7.92 (1H, d, J=8.8 Hz), 7.56 (1H, d, J+8.8 Hz), 6.61 (3H, s), 4.91-4.71 (2H, m), 3.75 (1H, m), 3.35 (3H, s), 1.16 (3H, d, J=11.2 Hz). Analysis. Calculated for $C_{16}H_{20}N_4O_3 \cdot 1.5\ C_4H_4O_4 \cdot 0.5\ H_2O$: C, 52.90; H, 5.45; N, 11.22. Found: C, 52.71; H, 5.75; N, 11.05.

EXAMPLE 9

1-((S)-2-Aminopropyl)-1H-furo[2,3-g]indazole-7-carboxylic acid (2-hydroxypropyl)-amide This compound was prepared by following a procedure similar to that described in Example 5, but replacing ethanolamine in Step A with 1-aminopropan-2-ol to give, after deprotection, the fumarate salt: mp 190-191° C.; MS (ES) m/z 317 (M$^+$); $^1$H NMR (DMSO-d$_6$) δ 8.65 (1H, t, J=2.6 Hz), 8.28 (1H, s), 8.23 (1H, s), 7.85 (1H, d, J=9.2 Hz), 7.50 (1H, d, J=9.2 Hz), 6.61 (1H, s), 4.70-4.54 (2H, m), 3.83 (1H, m), 3.54 (1H, m), 3.32-3.24 (2H, m), 1.11 (3H, d, J=6.4 Hz), 1.05 (3H, d, J=6.4 Hz). Analysis. Calculated for $C_{16}H_{20}N_4O_3 \cdot 0.7\ C_4H_4O_4$: C, 56.79; H, 5.78; N, 14.09. Found: C, 56.42; H, 5.79; N, 14.39.

EXAMPLE 10

1-((S)-2-Aminopropyl)-1H-furo[2,3-g]indazole-7-carboxylic acid (1-hydroxy-cyclopropylmethyl)-amide This compound was prepared by following a procedure similar to that described in Example 5, but replacing ethanolamine in Step A with 1-aminomethyl-cyclopropanol to give, after deprotection, the fumarate salt: mp 77-79° C.; LC/MS m/z 329 [M+H]$^+$; $^1$H NMR (D$_2$O) δ 8.12 (d, J=1.8 Hz, 1H), 7.74 (dd, J=8.4, 1.8 Hz, 1H), 7.68 (s, 1H), 7.35 (d, J=8.4 Hz, 1H), 6.62 (s, 2H), 4.67 (m, 2H), 3.89 (m, J=6.0 Hz, 1H), 3.52 (s, 2H), 1.23 (d, J=6.6 Hz, 3H), 0.74 (m, 2H), 0.67 (m, 2H). Analysis. Calculated for $C_{17}H_{20}N_4O_3 \cdot C_4H_4O_4 \cdot 1.5\ H_2O \cdot 0.5\ CH_4O$: C, 52.38; H, 5.74; N, 10.86. Found: C, 52.27; H, 5.38; N, 10.89.

EXAMPLE 11

1-((S)-2-Aminopropyl)-1H-furo[2,3-g]indazole-7-carboxylic acid (3-hydroxy-2,2-dimethyl-propyl)-amide This compound was prepared by following a procedure similar to that described in Example 5, but replacing ethanolamine in Step A with 3-amino-2,2-dimethylpropanol to give, after deprotection, the fumarate salt: mp 103° C.; LC/MS m/z 345 [M+H]$^+$; $^1$H NMR (D$_2$O): δ 8.12 (s, 1H), 7.75 (d, J=9.0 Hz, 1H), 7.65 (s, 1H), 7.34 (d, J=9.0 Hz, 1H), 6.65 (s, 2.8H), 4.67 (m, 2H), 3.91 (s, 1H), 3.34 (s, 2H), 3.29 (s, 2H), 3.26 (s, 2H), 1.24 (d, J=7.2 Hz, 3H), 0.90 (s, 6H). Analysis. Calculated for $C_{18}H_{24}N_4O_3 \cdot 1.5\ C_4H_4O_4 \cdot 0.5\ H_2O \cdot 0.5\ CH_4O$: C, 54.14; H, 6.12; N, 10.31. Found: C, 54.10; H, 6.02; N, 10.47.

EXAMPLE 12

1-((S)-2-Amino-propyl)-1H-furo[2,3-g]indazole-7-carboxylic acid (3-acetylaminopropyl)-amide This compound was prepared by following a procedure similar to that described in Example 5, but replacing ethanolamine in Step A with N-(3-aminopropyl)-acetamide to give, after deprotection, the fumarate salt: mp 81° C.; LC/MS m/z 358 [M+H]$^+$; $^1$H NMR (D$_2$O, 600 MHz): δ 8.22 (s, 1H), 7.85 (d, J=9.0 Hz, 1H), 7.78 (s, 1H), 7.46 (dd, J=9.0, 0.6 Hz, 1H), 6.69 (s, 2H), 4.78 (m, 2H), 4.00 (m, 1H), 3.47 (t, J=6.6 Hz, 2H), 3.29 (t, J=6.6 Hz, 2H), 1.98 (s, 3H), 1.86 (hept, J=6.6 Hz, 2H), 1.32 (d, J=7.2 Hz, 3H). Analysis. Calculated for $C_{18}H_{23}N_5O_3 \cdot 1.25\ C_4H_4O_4 \cdot H_2O$: C, 53.07; H, 5.81; N, 13.46. Found: C, 52.90; H, 5.65; N, 13.43.

Example 13

1-((S)-2-Aminopropyl)-1H-furo[2,3-g]indazole-7-carboxylic acid [3-(2-oxo-pyrrolidin-1-yl)-propyl]-amide This compound was prepared by following a procedure similar to that described in Example 5, but replacing ethanolamine in Step A with 1-(3-aminopropyl)-pyrrolidin-2-one to give, after deprotection, the fumarate salt: mp 82° C.; LC/MS m/z 384 [M+H]$^+$; $^1$H NMR (D$_2$O): δ 8.26 (s, 1H), 7.89 (d, J=9.0 Hz, 1H), 7.81 (s, 1H), 7.50 (d, J=9.0 Hz, 1H), 6.78 (s, 3.4H), 4.82 (m, 2H), 4.05 (m, 1H), 3.57 (t, J=7.2 Hz, 2H), 3.47 (t, J=7.2 Hz, 2H), 3.43 (t, J=7.2 Hz, 2H), 2.45 (t, J=7.8 Hz, 2H), 2.07 (m, 2H), 1.96 (m, 2H), 1.36 (d, J=6.6 Hz, 3H). Analysis. Calculated for $C_{20}H_{25}N_5O_3 \cdot 1.8\ C_4H_4O_4 \cdot 0.5\ H_2O$: C, 54.08; H, 5.53; N, 11.43. Found: C, 54.03; H, 5.58; N, 11.43.

EXAMPLE 14

1-((S)-2-Aminopropyl)-1H-furo[2,3-g]indazole-7-carboxylic acid (5-methyl-furan-2-ylmethyl)amide This compound was prepared by following a procedure similar to that described in Example 5, but replacing ethanolamine in Step A with (5-methyl-furan-2-yl)-methylamine to give, after deprotection, the fumarate salt: mp 118-120° C.; LC/MS m/z 353 [M+H]$^+$; $^1$H NMR (D$_2$O): δ 8.12 (s, 1H), 7.76 (d, J=9.0 Hz, 1H), 7.65 (d, J=0.6 Hz, 1H), 7.33 (dd, J=9.0, 0.6 Hz, 1H), 6.65 (s, 2.2H), 6.27 (d, J=3.0 Hz, 1H), 6.02 (d, J=1.8 Hz, 1H), 4.67 (t, J=6.6 Hz, 2H), 4.67 (t, J=6.6 Hz, 2H), 4.50 (s, 2H), 3.92 (m, 1H), 2.24 (s, 3H), 1.27 (d, J=6.6 Hz, 3H). Analysis. Calculated for $C_{19}H_{20}N_4O_3 \cdot 1.25\ C_4O_4 \cdot H_2O$: C, 55.92; H, 5.28; N, 10.87. Found: C, 56.19; H, 5.26; N, 10.83.

EXAMPLE 15

(S)-1-Methyl-2-[7-(3-methyl-1,2,4-oxadiazol-5-yl)-furo[2,3-g]indazol-1-yl]-ethylamine Step A: 1-((S)-2-Aminopropyl)-1H-furo[2,3-g]indazole-7-carboxylic acid methyl ester To a 50 mL round bottom flask containing NMP (20 mL), methyl bromoacetate (0.35 g 2.3 mmol), and [2-(7-formyl-6-hydroxy-indazol-1-yl)-1-methyl-ethyl]-carbamic acid benzyl ester (0.751 g, 2.1 mmol) was added $K_2CO_3$ (1.4 g, 10 mmol). This mixture was heated to 90° C. for 16 h, then allowed to cool to 23° C., decanted into a saturated aqueous $NaHCO_3$ solution (50 mL), and extracted with ethyl acetate (2×20 mL). The combined extracts were dried ($Na_2SO_4$), filtered and concentrated. The crude product was purified by chromatography (silica gel, hexanes: ethyl acetate gradient, 3:1 to 1:1) to provide an oil: LC/MS m/z 408 [M+H]$^+$; $^1$H NMR ($D_2O$): δ 8.19 (s, 1H), 8.06 (s, 1H), 7.75 (d, J=9.0 Hz, 1H), 7.43 (d, J=9.0 Hz, 1H), 7.30 (bm, 4H), 5.15 (d, 1H), 5.08 (dd, 2H), 4.8 (m, 1H), 4.6 (m, 1H), 4.29 (m, 1H), 4.01 (s, 3H), 1.19 (d, J=6.6 Hz, 3H).

Step B: (S)-1-Methyl-2-[7-(3-methyl-1,2,4-oxadiazol-5-yl)-furo[2,3-g]indazol-1-yl]-ethylamine fumarate To a 50 mL round bottom flask containing THF (5 mL), molecular sieves (0.80 g), sodium hydride (0.040 g, 1.0 mmol; 60% in mineral oil, washed with hexanes) and acetamide oxime (0.07 g, 1.0 mmol). This mixture was heated to 50° C. for 1 h. The product from Step A (0.20 g, 0.50 mmol) was added and the mixture heated at reflux temperature for 2.5 h, then allowed to cool to 23° C., decanted into a saturated aqueous $NaHCO_3$ solution (50 mL), and extracted with dichloromethane (2×20 mL). The combined extracts were washed with a saturated aqueous $NaHCO_3$ solution (50 mL), dried ($Na_2SO_4$), filtered and concentrated. The crude product was purified by chromatography (silica gel, methanol: dichloromethane gradient, 4% to 8%) to furnish the free base (0.049 g, 32%). Fumaric acid (0.019 g, 0.16 mmol) was added to a solution of the free base in methanol (3 mL) concentration of the mixture provided the salt: mp 187-9° C.; LC/MS m/z 298 [M+H]$^+$; $^1$H NMR ($D_2O$): δ 7.98 (d, J=3.0 Hz, 1H), 7.78 (s, 1H), 7.66 (d, J=8.4 Hz, 1H), 7.30 (d, J=8.4 Hz, 1H), 6.52 (s, 2.4H), 4.58 (m, 2H), 3.83 (m, 1H), 2.27 (s, 3H), 1.19 (d, J=6.6 Hz, 3H). Analysis. Calculated for $C_{15}H_{15}N_5O_2 \cdot 1.2\ C_4H_4O_4 \cdot 0.7\ H_2O$: C, 52.94; H, 4.76; N, 15.59. Found: C, 53.07; H, 4.71; N, 15.61.

EXAMPLE 16

2-[1-((S)-2-Amino-propyl)-1H-furo[2,3-g]indazol-7-yl]-N-methyl-acetamide

Step A: [(S)-2-(7-Cyanomethyl-furo[2,3-g]indazol-1-yl)-1-methylethyl]-carbamic acid benzyl ester A solution of the product from Example 2, Step B (0.55 g, 1.45 mmol) in dichloromethane (20 mL) was cooled (ice bath), thionyl chloride (0.16 mL, 2.18 mmol) was added, and the mixture was stirred for thirty minutes. The reaction mixture was evaporated to a residue which was dissolved in dichloromethane (20 mL) and evaporated. A solution of sodium cyanide (0.29 g, 5.8 mmol) in DMSO (10 mL) was added to this residue and the mixture was stirred at room temperature for one hour. Saturated aqueous sodium bicarbonate (100 mL) was added and the mixture was extracted with ethyl acetate (3×100 mL). The combined extracts were washed with saturated aqueous sodium bicarbonate (2×150 mL), dried ($MgSO_4$) and evaporated to a tan solid (0.49 g, 87%): LC/MS m/z 389 [M+H]$^+$.

Step B: [1-((S)-2-Aminopropyl)-1H-furo[2,3-g]indazol-7-yl]-acetic acid methyl ester The product from Step A (0.48 g, 1.24 mmol) was added to double distilled 20% aqueous hydrochloric acid (5 mL) and heated at 90° C. for one hour and evaporated to a residue, which was treated with dry methanolic hydrochloric acid (0.5 N, 5 mL) at room temperature overnight. The reaction was evaporated to give the methyl ester (0.25 g, 61%): LC/MS m/z 288 [M+H]$^+$.

Step C: 2-[1-((S)-2-Amino-propyl)-1H-furo[2,3-g]indazol-7-yl]-N-methyl-acetamide The product from Step B (0.25 g, 0.77 mmol) was combined with 2 M methanolic methylamine (10 mL, 20 mmol) and the mixture was stirred at room temperature overnight. The reaction mixture was evaporated and the residue purified by reversed phase chromatography (gradient, water/acetonitrile with 0.1% TFA). Evaporation of selected fractions gave an oil (0.15 g; LC/MS 287 m/z) that was treated with methanolic hydrochloric acid (0.5 N, 5 mL) and evaporated to give the methyl amide as an amorphous solid (0.15 g, 60%): LC/MS m/z 287 [M+H]$^+$; $^1$H NMR ($CD_3OD$) δ 8.167 (s, 1H), 7.65 and 7.39 (ABq, 2H, J=9Hz), 7.22 (s, 1H), 4.80 (d, 2H, J=6 Hz), 3.97 (m, 1H, J=6 Hz, J=7 Hz), 3.85 (s, 2H), 2.81 (s, 3H), 1.34 (d, 3H, 7 Hz). Analysis. Calculated for $C_{15}H_{18}N_4O_2 \cdot 2\ HCl \cdot 1.2\ H_2O$: C, 52.31; H, 6.26; N, 16.27. Found: C, 52.61; H, 6.12; N, 15.93.

EXAMPLE 17

N-[1-((S-2-Aminopropyl)-1H-furo[2,3-g]indazol-7-ylmethyl]-nicotinamide

Step A: [(S)-2-(7-Azidomethyl-furo[2,3-g]indazol-1-yl)-1-methylethyl]-carbamic acid benzyl ester A suspension of the product from Example 3, Step B (2.80 g, 7.39 mmol) in dichloromethane (30 mL) was cooled (ice bath), thionyl chloride (0.81 mL, 11.1 mmol) was added and the mixture was stirred for 30 minutes. During the reaction the white suspension dissolved to a yellow solution and then became a white suspension. The reaction was evaporated. The residue was treated with a solution of sodium azide (5 eq, 37 mmol, 2.4 g) in DMSO (40 mL, heated at 70° C. to dissolve) with stirring and let cool to room temperature for 20 minutes. The reaction was quenched with saturated aqueous sodium bicarbonate (100 mL) and extracted with dichloromethane (200 mL). The organic layer was washed with brine (100 mL), dried ($MgSO_4$) and evaporated to give a yellow oil, 2.84 g. This residue was purified by chromatography (silica gel, hexane/ethyl acetate gradient) to give a colorless waxy residue, 2.45 g (82%) LC/MS m/z 405 [M+H]$^+$.

Step B: [(S)-2-(7-Aminomethyl-furo[2,3-g]indazol-1-yl)-1-methylethyl]-carbamic acid benzyl ester A solution of the product from Step A (1.28 g, 3.17 mmol) in THF (25 mL) was stirred with polymer supported triphenylphosphine (4 eq, 3 mmol/g, 12.7 mmol, 4.23 g) at 50° C. for 2 hours. Water (2.5 mL) was added and the mixture was stirred for another hour; more water (5 mL) was added and the reaction mixture was filtered. The solids were washed well with THF and the filtrate was evaporated to a residue which was dried under a vacuum to give a foam (1.10 g, 92%): LC/MS m/z 379 [M+H]$^+$.

Step C: [(S)-1-Methyl-2-(7-{[(pyridine-3-carbonyl)-amino]-methyl}-furo[2,3-g]indazol-1-yl)-ethyl]-carbamic acid benzyl ester To a solution of the product from Step B (0.32 g, 0.847 mmol) in THF (20 mL) was added polymer supported di-isopropyl ethyl amine (3.86 mmol/g, 0.44 g, 1.69 mmol, 2 eq); this suspension was cooled (ice bath) and nicotinoyl chloride (0.15 g, 0.847 mmol) was added. The ice bath was removed and mixture was stirred for one hour, additional nicotinoyl chloride (50 mg) was added and the mixture was stirred at room temperature overnight. Triethylamine was added and after stirring for 10 min saturated aqueous sodium bicarbonate (150 mL) was added. This mixture was extracted with ethyl acetate (2×100 mL). The combined extracts were dried (MgSO$_4$) and evaporated to an oil which was purified by chromatography (silica gel, hexane/ethyl acetate gradient) to give a solid (0.16 g, 39%): LC/MS m/z 484 [M+H]$^+$.

Step D: N-[1-((S)-$^2$-Aminopropyl)-1H-furo[2,3-g]indazol-7-ylmethyl]-nicotinamide To a solution of the product from Step C (0.16 g, 0.33 mmol) in methanol (20 mL) was added 10% Palladium on carbon (20 mg) and this mixture was stirred under an atmosphere of hydrogen at room temperature for two days. The reaction mixture was filtered and the filtrate evaporated to give a colorless oil (0.10 g, 87%): LC/MS m/z 350 [M+H]$^+$; $^1$H NMR (CD$_3$OD) δ 9.052 (s, 1H), 8.70 (m, 1H), 8.31 (m, 1H), 8.08 (s, 1H), 7.62 and 7.36 (ABq, J=9 Hz, 2H), 7.56 (m, 1H), 4.50 (overlapping m and s, 4H), 3.47 (m, 1H), 1.08 (d, 3H).

EXAMPLE 18

1-[1-((S)-2-Aminopropyl)-1H-furo[2,3-g]indazol-7-ylmethyl]-3-ethylurea

Step A: ((S)-2-{7-[(3-Ethylureido)-methyl]-furo[2,3-g]indazol-1-yl}-1-methylethyl)-carbamic acid benzyl ester To a solution of the product from Example 17, Step B (0.20 g, 0.53 mmol) in THF (4 mL) was added polymer supported di-isopropylamine (1.5 eq, 0.79 mmol, 0.22 g) and ethyl isocyanate (0.042 mL, 0.52 mmol); this mixture was stirred at room temperature for three hours followed by the addition of methanol (5 mL). Dichloromethane (15 mL) was added and the mixture was filtered, evaporation of the filtrate gave a solid (0.19 g) which was purified by chromatography (silica gel, hexane/ethyl acetate gradient) to give a white solid (0.14 g, 59%): LC/MS m/z 450 [M+H]$^+$.

Step B: 1-[1-((S)-2-Aminopropyl)-1H-furo[2,3-g]indazol-7-ylmethyl]-3-ethylurea Reaction of the product from Step A in a manner similar to that described in Example 17, Step D gave a colorless oil (98 mg: LC/MS m/z 316 [M+H]$^+$; $^1$H NMR (CD$_3$OD) δ 7.97 (d, 1H), 7.49 and 7.23 (ABq, J=9 Hz, 2H), 7.02 (s, 1H), 4.43 (s, 2H), 4.41 (m, 2H), 3.41 (m, J=6 Hz, 1H), 3.08 (q, J=7 Hz, 2H), 1.01 (overlapping d and t, J=6 Hz and 7 Hz, 6H).

EXAMPLE 19

N-(4-{[1-((S)-2-Aminopropyl)-1H-furo[2,3-g]indazol-7-ylmethyl]-sulfamoyl}-phenyl)-acetamide

Step A: ((S)-2-{7-[(4-Acetylamino-benzenesulfonylamino)-methyl]-furo[2,3-g]indazol-1-yl}-1-methylethyl)-carbamic acid benzyl ester A solution of the product from Example 17, Step B (0.32 g, 0.85 mmol) in THF (10 mL) containing triethylamine (3.39 mmol, 0.47 mL) was cooled (ice bath) and N-acetylsulfanilyl chloride (0.20 g, 0.85 mmol) was added followed by stirring for one hour. The reaction mixture was warmed to room temperature, water (1 mL) was added, and stirring continued until all the solids dissolved. Saturated aqueous sodium bicarbonate (150 mL) was added and the mixture was extracted with ethyl acetate (2×100 mL). The combined extracts were washed with brine (100 mL), dried (MgSO$_4$) and evaporated to a residue which was purified by chromatography (silica gel, hexane/ethyl acetate gradient) to give an amorphous solid (0.32 g, 66%): LC/MS m/z 576 [M+H]$^+$.

Step B: N-(4-{[1-((S)-2-Aminopropyl)-1H-furo[2,3-g]indazol-7-ylmethyl]-sulfamoyl}-phenyl)-acetamide Reaction of the product from Step A in a manner similar to that described in Example 17, Step D gave a colorless solid (0.23 g, 94%): mp 80-85° C.; LC/MS m/z 442 [M+H]$^+$; $^1$H NMR (CD$_3$OD) δ 7.93 (s, 1H), 7.53 and 7.32 (ABq, 4H, 7 Hz), 7.45 and 7.08 (ABq, 2H, 9 Hz), 6.79 (s, 1H), 4.28 (overlapping m and s, 4H), 3.29 (m, 1H, 6 Hz), 1.94 (s, 3H), 0.97 (d, 3H, 6 Hz) Analysis. Calculated for C$_{21}$H$_{23}$N$_5$O$_4$S.0.4 H$_2$O: C, 56.21; H, 5.35; N, 15.61. Found: C, 56.50; H, 5.31; N, 15.25.

EXAMPLE 20

(S)-1-Methyl-2-[7-(4-pyridin-2-yl-piperazin-1-ylmethyl)-furo[2,3-g]indazol-1-yl]-ethylamine

Step A: {(S)-1-Methyl-2-[7-(4-pyridin-2-yl-piperazin-1-ylmethyl)-furo[2,3-g]indazol-1-yl]-ethyl}-carbamic acid benzyl ester A solution of the product from Example 3, Step B (0.18 g, 0.475 mmol) in dichloromethane (20 mL) was cooled (ice bath) and thionyl chloride (0.052 mL, 0.71 mmol) added. The mixture was stirred for 30 min and then evaporated to a residue which was dissolved in dichloromethane (20 mL); this solution was evaporated and the residue dried under a vacuum. The residue was dissolved in dichloromethane (20 mL) and 1-(2-pyridyl)piperazine (0.5 mL, 3.4 mmol) was added, and the mixture was stirred at room temperature for one hour at which point additional 1-(2-pyridyl)piperazine (0.9 mL) was added. Solvent was removed by evaporation (45° C.) and THF (10 mL) was added, followed by heating the mixture at reflux temperature for one hour. This reaction mixture was evaporated and the residue dissolved in methanol (25 mL) and triethylamine (1.5 mL) followed by evaporation of this mixture to a residue which was purified by chromatography (silica gel, hexane/ethyl acetate) to give a foamy solid (0.21 g, 84%): LC/MS m/z 525 [M+H]$^+$.

Step B: (S)-1-Methyl-2-[7-(4-pyridin-2-yl-piperazin-1-ylmethyl)-furo[2,3-g]indazol-1-yl]-ethylamine Reaction of the product from Step A in a manner similar to that described in Example 17, Step D gave a colorless oil (0.15 g, 96%): LC/MS m/z 391 [M+H]$^+$; $^1$H NMR (CD$_3$O) δ 7.97 (s, 2H), 7.52 (d, J=8 Hz, 1H), 7.43 (m, 1H), 7.62 and 6.69 (ABq, J=9 Hz, 2H), 7.18 (s, 1H), 6.56 (m, 1H), 4.39 (m, 2H), 3.75 (s, 2H), 3.44 (m, 4H), 3.36 (m, 1H), 2.61 (br, 4H), 0.98 (d, J=7 Hz, 3H). Analysis. Calculated for $C_{22}H_{26}N_6O \cdot 0.6$ $H_2O$: C, 65.85; H, 6.83; N, 20.94. Found: C, 65.95; H, 6.85; N, 20.58.

The compounds of the present invention can be used to lower and control IOP including IOP associated with normotension glaucoma, ocular hypertension, and glaucoma in warm blooded animals including humans and other mammals. Since the treatment of glaucoma is preferably with compounds that do not enter the CNS, relatively polar compounds that are 5-HT$_2$ agonists are of particular interest. The compounds are preferably formulated in pharmaceutical compositions which are preferably suitable for topical delivery to the eye of the patient.

The compounds of this invention, Formula A, can be incorporated into various types of pharmaceutical compositions, such as ophthalmic formulations for delivery to the eye (e.g., topically, intracamerally; or via an implant). The compounds are preferably incorporated into topical ophthalmic formulations for delivery to the eye. The compounds may be combined with ophthalmologically acceptable preservatives, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations; preservatives and tonicity agents can be incorporated.

The compounds are preferably formulated as topical ophthalmic suspensions or solutions, with a pH of about 5 to 8. The compounds will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), $\alpha_1$ antagonists (e.g., nipradolol), $\alpha_2$ agonists (e.g. iopidine and brimonidine), miotics (e.g., pilocarpine and epinephrine), prostaglandin analogs (e.g., latanoprost, travoprost, unoprostone, and compounds set forth in U.S. Pat. Nos. 5,889,052; 5,296,504; 5,422,368; and 5,151,444, "hypotensive lipids" (e.g., bimatoprost and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 60/203,350, and appropriate compounds from WO 94/13275, including memantine.

In the formulas described above, the alkyl group can be straight-chain, branched or cyclic and the like. Halogen includes Cl, Br, F, or I. Alkoxy is understood as an alkyl group bonded through an oxygen atom.

The compounds of the present invention preferably function as 5-HT$_2$ agonists and preferably do not enter the CNS. Compounds having the ability to be a 5-HT$_2$ agonist are beneficial for controlling IOP as well as the treatment of glaucoma as shown in International Published Patent Application No. WO 00/16761, incorporated in its entirety by reference herein.

The compounds of the present invention preferably provide increased chemical stability and preferably achieve the desired level of therapeutic activity which includes a lowering or controlling of IOP.

The compounds of the present invention can be used in controlling or lowering IOP in warm blooded animals including humans. Preferably, an effective amount of the compound is administered to the patient such that the IOP is controlled or lowered to acceptable levels. Furthermore, the compounds of the present invention can be used to treat glaucoma in warm blooded animals, including humans, by administering an effective amount of the compound to a patient in need of such treatment to treat the glaucoma. Pharmaceutically acceptable amounts of the compounds of the present invention will be readily understood by those skilled in the art to mean amounts sufficient to effect the desired therapy without toxicity or other deleterious effects on the patients' health. Examples of such amounts include without limitation those amounts shown in the Examples.

Another embodiment of the present invention is a method of activating or binding serotonin receptors, comprising administering an effective amount of at least one compound of the present invention to a patient using an amount effective to activate or bind serotonin receptors, wherein such amount includes, but is not limited to, the dosage levels described herein.

The procedures described herein in Method 1 can be used to confirm a compound's 5-HT$_2$ binding affinity.

Method 1

5-HT$_2$ Receptor Binding Assay

To determine the affinities of serotonergic compounds at the 5-HT$_2$ receptors, their ability to compete for the binding of the agonist radioligand [$^{125}$I]DOI to brain 5-HT$_2$ receptors is determined as described below with minor modification of the literature procedure [Neuropharmacology, 26, 1803 (1987)]. Aliquots of post mortem rat or human cerebral cortex homogenates (400 μL) dispersed in 50 mM TrisHCl buffer (pH 7.4) are incubated with [$^{125}$I]DOI (80 pM final) in the absence or presence of methiothepin (10 μM final) to define total and non-specific binding, respectively, in a total volume of 0.5 mL. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program [Trends Pharmacol. Sci., 16, 413 (1995)] to determine the compound affinity parameter. The concentration of the compound needed to inhibit the [$^{125}$I]DOI binding by 50% of the maximum is termed the IC$_{50}$ or K$_i$ value.

Method 2

5HT$^2$ Functional Assay: [Ca$^{2+}$]$_i$ Mobilization

The receptor-mediated mobilization on intracellular calcium ([Ca$^{2+}$]$_i$) was studied using the Fluorescence Imaging Plate Reader (FLIPR) instrument. Rat vascular smooth muscle cells, A7r5, were grown in a normal media of DMEM/10% FBS and 10 μg/mL gentamycin. Confluent cell monolayers were trypsinized, pelleted, and re-suspended in normal media. Cells were seeded in a 50 μL volume at a density of 20,000 cells/well in a black wall, 96-well tissue culture plate and grown for 2 days.

On the day of the experiment, one vial of FLIPR Calcium Assay Kit dye was re-suspended in 50 mL of a FLIPR buffer consisting of Hank's Balanced Salt Solution (HBSS), 20 mM HEPES, and 2.5 mM probenecid, pH 7.4. Cells were loaded with the calcium-sensitive dye by addition of an equal volume (50 μL) to each well of the 96-well plate and incubated with dye for 1 h at 23° C.

Typically, test compounds were stored at 25 μM in 50% DMSO/50% Ethanol solvent. Compounds were diluted 1:50 in 20% DMSO/20% Ethanol. For "hit" screening, compounds were further diluted 1:10 in FLIPR buffer and tested at a final concentration of 10 μM. For dose-response experiments, compounds were diluted 1:50 in FLIPR buffer and serially diluted 1:10 to give a 5- or 8-point dose-response curve.

The compound plate and cell plate were placed in the FLIPR instrument. At the beginning of an experimental run, a signal test was performed to check the basal fluorescence signal from the dye-loaded cells and the uniformity of the signal across the plate. The basal fluorescence was adjusted between 8000-12000 counts by modifying the exposure time, the camera F-stop, or the laser power. Instrument settings for a typical assay were the following: laser power 0.3-0.6 W, camera F-stop F/2, and exposure time 0.4 sec. An aliquot (25 μL) of the test compound was added to the existing 100 μL dye-loaded cells at a dispensing speed of 50 μL/sec. Fluorescence data were collected in real-time at 1.0 sec intervals for the first 60 secs and at 6.0 sec intervals for an additional 120 secs. Responses were measured as peak fluorescence intensity minus basal and where appropriate were expressed as a percentage of a maximum 5-HT-induced response [E$_{max}$%]. When the compounds were tested as antagonists against 10 μM 5-HT, they were incubated with the cells for 15 minutes prior to the addition of 5-HT.

Using the foregoing methods, 5-HT$_2$ binding affinities and agonist potential can readily be determined.

The above procedures were used to generate the data shown in Table 1.

TABLE 1

5-HT$_{2A}$ Receptor Binding and Functional Data

| Example | 5HT$_{2A(rat)}$ IC$_{50}$, nM | 5-HT$_{2A(rat)}$ EC$_{50}$, nM (E$_{max}$) | E$_{max}$ (%) |
|---|---|---|---|
| 1 | 0.21 | 63 | 101 |
| 2 | 0.53 | 18 | 86 |
| 3 | 2.3 | 158 | 87 |
| 4 | 0.81 | 54 | 98 |
| 5 | 3.5 | 55 | 94 |
| 6 | 0.66 | 57 | 95 |
| 7 | 1.3 | 109 | 89 |
| 8 | 2.3 | 54 | 94 |
| 9 | 1.5 | 27 | 98 |
| 10 | 1.1 | 15 | 94 |
| 11 | 1.8 | 74 | 76 |
| 12 | 1.4 | 37 | 95 |
| 13 | 2.0 | 72 | 87 |
| 14 | 0.3 | 181 | 94 |
| 15 | 0.9 | 283 | 101 |
| 16 | 0.7 | 28 | 97 |
| 17 | 3.0 | 22 | 95 |
| 18 | 4.1 | 23 | 87 |
| 19 | 4.1 | 131 | 82 |
| 20 | — | 141 | 81 |
| 5-HT | 0.9 | 56 | 101 |

TABLE 2

IOP Response in Conscious Cynomolgus Monkeys

| | Dose, | | Percent IOP Reduction ± SEM Hours after Dose | | |
|---|---|---|---|---|---|
| Example | μg | Baseline IOP (mmHg) | 1 | 3 | 6 |
| 3 | 300 | 32.8 | 9 ± 4 | 23 ± 4 | 27 ± 5 |
| 4 | 300 | 34.9 | 13 ± 3 | 30 ± 4 | 31 ± 4 |
| 11 | 300 | 37.8 | 10 ± 5 | 23 ± 5 | 26 ± 5 |
| (R)-DOI | 100 | 31.9 | 11 ± 5 | 25 ± 3 | 34 ± 5 |

IOP was determined with an Alcon Pneumatonometer after light corneal anesthesia with 0.1% proparacaine. Eyes were washed with saline after each measurement. After a baseline IOP measurement, test compound was instilled in one 30 μL aliquot to the right eyes only of nine cynomolgus monkeys. Vehicle was instilled in the right eyes of six additional animals. Subsequent IOP measurements were taken at 1, 3, and 6 hours.

The following topical ophthalmic formulations are useful according to the present invention administered 1-4 times per day according to the discretion of a skilled clinician.

EXAMPLE 21

| Ingredients | Amount (wt %) |
|---|---|
| Compound of Example 4 | 0.01-2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 22

| Ingredients | Amount (wt %) |
|---|---|
| Compound of Example 4 | 0.01-2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 23

| Ingredients | Amount (wt %) |
|---|---|
| Compound of Example 3 | 0.01-2% |
| Guar gum | 0.4-6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 24

| Ingredients | Amount (wt %) |
|---|---|
| Compound of Example 11 | 0.01-2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |

Other embodiments of the present invention will be apparent to those skilled in the art from consideration of the present specification and practice of the present invention disclosed herein. For example, it is understood that any of the compounds of the present invention may be formulated in the manner described in any of Examples 21-24. It is intended that the present specification and examples be considered as exemplary only with a true scope and spirit of the invention being indicated by the following claims and equivalents thereof.

What is claimed is:

1. A method of treating glaucoma or lowering or controlling intraocular pressure in a subject comprising administering to the subject a compound represented by the following Formula A:

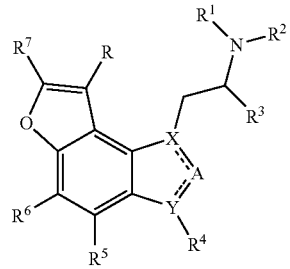

wherein R, $R^1$ and $R^2$ are independently chosen from hydrogen, $C_{1-4}$alkyl;

$R^3$ is selected from hydrogen, $C_{1-4}$alkyl, or $R^2$ and $R^3$ can complete a pyrrolidine or piperidine ring, which can be substituted with $C_{1-4}$alkyl;

$R^4$ is hydrogen, halogen, $C_{1-4}$alkyl;

$R^5$ and $R^6$ are independently chosen from hydrogen, halogen, $C_{1-6}$alkyl, $C_{1-6}$alkylthio, $C_{1-6}$alkylsulfonyl, $C_{1-6}$alkylsulfoxide, nitrile, $C_{1-6}$alkyl substituted with halogen;

$R^7$ is chosen from

C=$OR^9$;

$S(O)_m R^{10}$;

$NR^1$—(C=O)—$R^{11}$;

$C_{1-6}$alkyl substituted with hydroxyl, $C_{1-6}$alkoxy, OC(=O)$C_{1-8}$, $CO_2H$, $CO_2C_{1-6}$alkyl, C(=O)$NR^{12}R^{13}$, $S(O)_m NR^{12}R^{13}$, $NR^{14}R^{15}$, phenyl or a saturated or unsaturated 5 or 6-membered heterocyclic ring which can contain 1-4 heteroatoms selected from N, O, or S and can be unsubstituted or substituted with $C_{1-6}$alkyl, $C_{1-6}$alkoxy, halogen, halo$C_{1-4}$alkyl, phenyl or pyridinyl; or $R^7$ can be chosen from a heterocyclic ring selected from oxazol-2-yl; 4,5-dihydro-oxazol-2-yl; benzoxazol-2-yl; 5,6-dihydro-[1,3]oxazin-2-yl; thiazol-2-yl; 4,5-dihydro-thiazol-2-yl; benzothiazol-2-yl; imidazol-2-yl; imidazolidin-2-yl; [1,2,4]oxadiazol-5-yl; [1,2,4]oxadiazol-3-yl; [1,2,4]thiadiazol-5-yl; or [1,2,4]thiadiazol-3-yl, each of which can be unsubstituted or substituted with $C_{1-6}$alkyl, $C_{1-6}$alkoxy, phenyl, pyridinyl, or $C_{1-6}$alkyl substituted with phenyl or pyridinyl;

but $R^7$ cannot be hydrogen, lower alkyl, hydroxyl, lower alkoxy, amino, mono- or di-loweralkyl amino, lower alkanoylamino, or halogen;

$R^8$ is selected from $C_{1-6}$alkyl, phenyl which can be substituted with $C_{1-6}$alkyl, $C_{1-6}$alkoxy, $NR^1$(C=O)$C_{1-6}$alkyl, or halogen;

$R^9$ is chosen from hydroxyl; $C_{1-6}$alkoxy; $C_{1-6}$alkoxy substituted with phenyl or pyridinyl which can be substituted with $C_{1-4}$alkoxy or halogen; $NR^{16}R^{17}$; $C_{1-6}$alkyl; or $C_{1-6}$alkyl substituted with hydroxyl, $C_{1-6}$alkoxy, $NR^{12}R^{13}$, $CO_2H$, $CO_2C_{1-6}$alkyl, $S(O)_m NR^{12}R^{13}$, halogen, or phenyl or a heterocyclic ring selected from pyrrolidinyl, imidazoyl, morpholinyl, oxazolyl, isoxazolyl, thiazolyl, or tetrazolyl, or pyridinyl which can be unsubstituted or substituted with $C_{1-6}$alkyl, $C_{1-6}$alkoxy, halogen, halo$C_{1-4}$alkyl;

$R^{10}$ is chosen from $NR^{12}R^{13}$; $C_{1-6}$alkyl; $CH_2$phenyl or $CH_2$pyridinyl which can be substituted with $C_{1-6}$alkyl, $C_{1-6}$alkoxy, halogen, or halo$C_{1-4}$alkyl; or $C_{2-6}$alkyl substituted with hydroxyl, $C_{1-6}$alkoxy, $NR^{12}R^{13}$, $CO_2H$, $CO_2C_{1-6}$alkyl, phenyl, pyridinyl or imidazolyl which can be substituted with $C_{1-6}$alkyl, $C_{1-6}$alkoxy, halogen, halo$C_{1-4}$alkyl;

$R^{11}$ is $NH_2$; $NR^1R^2$; $C_{1-6}$alkyl substituted with hydroxyl, $C_{1-6}$alkoxy, $CO_2H$, $CO_2C_{1-6}$alkyl, phenyl or a saturated or unsaturated 5 or 6-membered heterocyclic ring which can contain 1-4 heteroatoms selected from N, O, or S and can be unsubstituted or substituted with $C_{1-6}$alkyl, $C_{1-6}$alkoxy, halogen, halo$C_{1-4}$alkyl;

$R^{12}$ and $R^{13}$ are independently selected from hydrogen; $C_{1-6}$alkyl; $CH_2Z$, where Z is selected from phenyl, pyridinyl, furanyl, thiophenyl, pyrimidinyl, pyrazinyl, or pyridazinyl, and which can be substituted with $C_{1-6}$alkyl, $C_{1-6}$alkoxy, halogen, or halo$C_{1-4}$alkyl; $C_{2-6}$alkyl substituted with hydroxyl, $C_{1-6}$alkoxy, $CO_2H$, $CO_2C_{1-6}$alkyl, $NR^1COC_{1-6}$alkyl, or halogen; or $R^{12}$, $R^{13}$, and the intervening nitrogen atom can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with $C_{1-4}$alkyl or $C_{1-4}$alkyl substituted with hydroxy, $C_{1-4}$alkoxy or halogen;

$R^{14}$ and $R^{15}$ are independently selected from hydrogen, $C_{1-6}$alkyl, hydroxyl, $C_{1-6}$alkoxy, (C=O)—$R^{11}$, $S(O)_m$$R^8$, phenyl or pyridinyl which can be substituted with $C_{1-6}$alkyl, $C_{1-6}$alkoxy, halogen, or halo$C_{1-4}$alkyl; or $R^{14}$, $R^{15}$ and the nitrogen atom to which they are attached can form a heterocyclic ring selected from pyrrolidine, piperazine, or piperidine, which can be substituted with $C_{1-6}$alkyl, phenyl, or pyridinyl;

$R^{16}$ and $R^{17}$ are independently selected from hydrogen; $C_{1-6}$alkyl; hydroxyl; $C_{1-6}$alkoxy; $CH_2Z$, where Z is selected from phenyl, pyridinyl, furanyl, thiophenyl, pyrimidinyl, pyrazinyl, or pyridazinyl, and which can be substituted with $C_{1-6}$alkyl, $C_{1-6}$alkoxy, halogen, or halo$C_{1-4}$alkyl; $C_{2-6}$alkyl substituted with hydroxyl, $C_{1-6}$alkoxy, halogen, $NR^1(C=O)C_{1-6}$alkyl, or a phenyl or a heterocyclic ring selected from pyrrolidin-2-yl; imidazo-2-yl; imidazo-4-yl; morpholin-3-yl; piperidin-4-yl; oxazolyl; isoxazolyl; thiazolyl; tetrazolyl; pyridinyl; each of which can be unsubstituted or substituted with $C_{1-6}$alkyl, $C_{1-6}$alkoxy, halogen, halo$C_{1-4}$alkyl, phenyl$C_{1-4}$alkyl, oxo (=O); or $R^{16}$, $R^{17}$, and the intervening nitrogen atom can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with $C_{1-4}$alkyl or $C_{1-4}$alkyl substituted with hydroxy, oxo (=O), $C_{1-4}$alkoxy, or phenyl;

m is 0-2;

A is N or CH; and

X and Y are either N or C, wherein X and Y cannot be the same; and the dashed bonds denote a suitably appointed single and double bond.

2. The method of claim 1, wherein for the compound of Formula A:

R, $R^1$ and $R^2$ are independently chosen from hydrogen, $C_{1-4}$alkyl;

$R^3$ is selected from hydrogen, $C_{1-4}$alkyl, or $R^2$ and $R^3$ can complete a pyrrolidine or piperidine ring, which can be substituted with $C_{1-4}$alkyl;

$R^4$ is hydrogen, $C_{1-4}$alkyl;

$R^5$ and $R^6$ are independently chosen from hydrogen, halogen, $C_{1-4}$alkyl, $C_{1-6}$alkylthio, $C_{1-6}$alkylsulfonyl, $C_{1-6}$alkylsulfoxide, nitrile, $C_{1-6}$alkyl substituted with halogen;

$R^7$ is chosen from

C=O$R^9$;

$C_{1-6}$alkyl substituted with hydroxyl; $C_{1-6}$alkoxy, OC(=O)$C_{1-8}$, $CO_2H$, $CO_2C_{1-6}$alkyl; C(=O) $NR^{12}R^{13}$, $S(O)_mNR^{12}R^{13}$, $NR^{14}R^{15}$, phenyl or a saturated or unsaturated 5 or 6-membered heterocyclic ring which can contain 1-4 heteroatoms selected from N, O, or S and can be unsubstituted or substituted with $C_{1-6}$alkyl; $C_{1-6}$alkoxy, halogen, halo$C_{1-4}$alkyl; phenyl or pyridinyl; or $R^7$ can be chosen from a heterocyclic ring selected from oxazol-2-yl; 4,5-dihydro-oxazol-2-yl; benzoxazol-2-yl; 5,6-dihydro-[1,3]oxazin-2-yl; thiazol-2-yl; 4,5-dihydro-thiazol-2-yl; benzothiazol-2-yl; imidazol-2-yl; imidazolidin-2-yl; [1,2,4]oxadiazol-5-yl; [1,2,4]oxadiazol-3-yl; [1,2,4]thiadiazol-5-yl; or [1,2,4]thiadiazol-3-yl, each of which can be unsubstituted or substituted with $C_{1-6}$alkyl, $C_{1-6}$alkoxy, phenyl, pyridinyl, or $C_{1-6}$alkyl substituted with phenyl or pyridinyl;

but $R^7$ cannot be hydrogen, lower alkyl, hydroxyl, lower alkoxy, amino, mono- or di-loweralkyl amino, lower alkanoylamino, or halogen;

$R^8$ is selected from $C_{1-6}$alkyl, phenyl which can be substituted with $C_{1-6}$alkyl, $C_{1-6}$alkoxy, $NR^1(C=O)C_{1-6}$alkyl, or halogen;

$R^9$ is chosen from hydroxyl; $C_{1-6}$alkoxy; $C_{1-6}$alkoxy substituted with phenyl or pyridinyl which can be substituted with $C_{1-4}$alkoxy or halogen; $NR^{16}R^{17}$; $C_{1-6}$alkyl; or $C_{1-6}$alkyl substituted with hydroxyl, $C_{1-6}$alkoxy, $NR^{12}R^{13}$, $CO_2H$, $CO_2C_{1-4}$alkyl, $S(O)_mNR^{12}R^{13}$, halogen, or phenyl or a heterocyclic ring selected from pyrrolidinyl, imidazoyl, morpholinyl, oxazolyl, isoxazolyl, thiazolyl, or tetrazolyl, or pyridinyl which can be unsubstituted or substituted with $C_{1-6}$alkyl, $C_{1-6}$alkoxy, halogen, halo$C_{1-4}$alkyl;

$R^{11}$ is $NH_2$; $NR^1R^2$; $C_{1-6}$alkyl substituted with hydroxyl, $C_{1-6}$alkoxy, $CO_2H$, $CO_2C_{1-6}$alkyl, phenyl or a saturated or unsaturated 5 or 6-membered heterocyclic ring which can contain 1-4 heteroatoms selected from N, O, or S and can be unsubstituted or substituted with $C_{1-6}$alkyl, $C_{1-6}$alkoxy, halogen, halo$C_{1-4}$alkyl;

$R^{12}$ and $R^{13}$ are independently selected from hydrogen; $C_{1-6}$alkyl; $CH_2Z$, where Z is selected from phenyl, pyridinyl, furanyl, thiophenyl, pyrimidinyl, pyrazinyl, or pyridazinyl, and which can be substituted with $C_{1-6}$alkyl, $C_{1-6}$alkoxy, halogen, or halo$C_{1-4}$alkyl; $C_{2-6}$alkyl substituted with hydroxyl, $C_{1-6}$alkoxy, $CO_2H$, $CO_2C_{1-6}$alkyl, $NR^1COC_{1-6}$alkyl, or halogen; or $R^{12}$, $R^{13}$, and the intervening nitrogen atom can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with $C_{1-4}$alkyl or $C_{1-4}$alkyl substituted with hydroxy, $C_{1-4}$alkoxy or halogen;

$R^{14}$ and $R^{15}$ are independently selected from hydrogen, $C_{1-6}$alkyl, hydroxyl, $C_{1-6}$alkoxy, (C=O)—$R^{11}$, $S(O)_m$$R^8$, phenyl or pyridinyl which can be substituted with $C_{1-6}$alkyl, $C_{1-6}$alkoxy, halogen, or halo$C_{1-4}$alkyl; or $R^{14}$, $R^{15}$ and the nitrogen atom to which they are attached can form a heterocyclic ring selected from pyrrolidine, piperazine, or piperidine, which can be substituted with $C_{1-6}$alkyl, phenyl, or pyridinyl;

R$^{16}$ and R$^{17}$ are independently selected from hydrogen; C$_{1-6}$alkyl; hydroxyl; C$_{1-6}$alkoxy; CH$_2$Z, where Z is selected from phenyl, pyridinyl, furanyl, thiophenyl, pyrimidinyl, pyrazinyl, or pyridazinyl, and which can be substituted with C$_{1-6}$alkyl, C$_{1-6}$alkoxy, halogen, or haloC$_{1-4}$alkyl; C$_{2-6}$alkyl substituted with hydroxyl, C$_{1-6}$alkoxy, halogen, NR$^1$(C=O)C$_{1-6}$alkyl, or a phenyl or a heterocyclic ring selected from pyrrolidin-2-yl; imidazo-2-yl; imidazo4-yl; morpholin-3-yl; piperidin-4-yl; oxazolyl; isoxazolyl; thiazolyl; tetrazolyl; pyridinyl; each of which can be unsubstituted or substituted with C$_{1-6}$alkyl, C$_{1-6}$alkoxy, halogen, haloC$_{1-4}$alkyl, phenylC$_{1-4}$alkyl, oxo (=O); or R$^{16}$, R$^{17}$, and the intervening nitrogen atom can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with C$_{1-4}$alkyl or C$_{1-4}$alkyl substituted with hydroxy, oxo (=O), C$_{1-4}$alkoxy, or phenyl;

m is 0-2;

A is N; and

X and Y are either N or C, wherein X and Y cannot be the same; and the dashed bonds denote a suitably appointed single and double bond.

3. The method of claim 2, wherein the compound of Formula A is:
   1-((S)-2-aminopropyl)-1H-furo[2,3-g]indazole-7-carboxylic acid amide;
   1-((S)-2-aminopropyl)-1H-furo[2,3-g]indazole-7-carboxylic acid methyl amide fumarate;
   1-((S)-2-aminopropyl)-1H-furo[2,3-g]indazole-7-carboxylic acid (1-hydroxy-cyclopropylmethyl)-amide; or
   1-((S)-2-aminopropyl)-1H-furo[2,3-g]indazole-7-carboxylic acid (3-hydroxy-2,2-dimethyl-propyl)-amide.

4. The method of claim 3, wherein the compound of Formula A is 1-((S)-2-aminopropyl)-1H-furo[2,3-g]indazole-7-carboxylic acid (3-hydroxy-2,2-dimethyl-propyl)-amide.

* * * * *